US005766877A

United States Patent [19]
Stark et al.

[11] Patent Number: 5,766,877
[45] Date of Patent: Jun. 16, 1998

[54] GENES ENCODING ART, AN AGOUTI-RELATED TRANSCRIPT

[75] Inventors: Kevin Lee Stark; Roland Luethy. both of Newbury Park, Calif.

[73] Assignee: Amgen Inc., Thousand Oaks, Calif.

[21] Appl. No.: 757,541

[22] Filed: Nov. 27, 1996

Related U.S. Application Data

[60] Provisional application No. 60/017,505, May 10, 1996.
[51] Int. Cl.[6] ................................................... C12N 15/12
[52] U.S. Cl. ............... 435/69.1; 536/23.5; 435/252.3; 435/254.11; 435/320.1; 435/325
[58] Field of Search ......................... 435/69.1, 325, 435/320.1, 252.3, 254.11; 536/23.5

[56] References Cited

U.S. PATENT DOCUMENTS

| 3,773,919 | 11/1973 | Boswell et al. | 424/19 |
| 5,252,714 | 10/1993 | Harris et al. | 530/391.9 |

FOREIGN PATENT DOCUMENTS

| 36676 | 3/1979 | European Pat. Off. |
| 52322 | 11/1981 | European Pat. Off. |
| 58481 | 1/1982 | European Pat. Off. |
| 143949 | 10/1984 | European Pat. Off. |
| 0 154 316 | 3/1985 | European Pat. Off. |
| 0 401 384 | 12/1989 | European Pat. Off. |
| 88046 | 2/1993 | European Pat. Off. |

OTHER PUBLICATIONS

Shutter, et al. Hypothalamic expression of ART, a novel gene related to agouti, is up–regulated in obese and diabetic mutant mice, *Genes & Development*, 11: 593–602 (1997).
A.G. Searle, *Comparative Genetics of Coat Color in Mammals*, Academic Press, New York, New York (1968), v–vii.
Bultman et al., Molecular Characterization of the Mouse Agouti Locus, *Cell*, 71: 1195–1204 (1992).
Takeuchi, Genetic Control of Signal Transduction in Mouse Melanocytes, *Journal Invest. Dermatology*, 92: 239S–242S (1989).
Jackson, Color–Coded Switches, *Nature*, 362: 587–588 (1993).
Lu et al., Agouti Protein is an Antagonist of the Melanocyte-stimulating Hormone Receptor, *Nature*, 371: 799–802 (1994).
Willard et al., Agouti Structure and Function: Characterization of a Potent α–Melanocyte Stimulating Hormone Receptor Antagonist, *Biochemistry*, 34: 12341–12346 (1995).
Wilson et al., Structure and Function of ASP, the Human Homolog of the Mouse Agouti Gene, *Human Molecular Genetics*, 4: 223–230 (1995).
Kwon et al., Molecular Structure and Chromosomal Mapping of the Human Homolog of the Agouti Gene. *Proc. Natl. Acad. Sci. USA*, 91: 9760–9764 (1994).
Manne et al., Mechanisms for the Pleiotropic Effects of the Agouti Gene, *Proc. Natl. Acad. Sci. USA*, 92: 4721–4724 (1995).

Klebig et al., Ectopic Expression of the Agouti Gene in Transgenic Mice Causes Obesity, Features of Type II Diabetes, and Yellow Fur, *Proc. Natl. Acad. Sci. USA*, 92: 4728–4732 (1995).
Ichida et al., Characteristics of Specific $^{125}$I–w–Conotoxin GVIA Binding in Rat Whole Brain, *Neurochemial Research*, 18: 1137–1144 (1993).
Figueriedo et al., Purification and Amino Acid Sequence of the Insecticidal Neurotoxin Tx4(6–1) from the Venom of the 'Armed' Spider Phoneutria Nigriventer, *Toxicon*, 33: 83–93 (1995).
Kim et al., Three–dimensional Solution Structure of the Calcium Channel Antagonist 2–Agatoxin IVA: Consensus Molecular Folding of Calcium Channel Blockers, *Journal of Molecular Biology*, 250: 659–671 (1995).
Mountjoy et al., The Cloning of a Family of Genes That Encode the Melanocortin Receptors, *Science*, 257: 1248–1251 (1992).
Roselli–Reyfuss et al., Identification of a Receptor for y melanotropin and Other Proopiomelanocortin Peptides in the Hypothalamus and Limbic System, *Proc. Natl. Acad. Sci. USA*, 90: 8856–8860 (1993).
Labbe et al., Molecular Cloning of a Mouse Melanocortin 5 Receptor Gene Widely Expressed in Peripheral Tissues, *Biochemistry*, 33: 4543–4549 (1994).
Qu et al., A Role for Melanin–concentrating hormone in the Central regulation of Feeding Behavior, *Nature*, 380: 243–247 (1996).
Dayhoff et al., *Atlas of Protein Sequence and Structure*, 5, supp. 3, (1978), vii–xix.
Sambrook et al., *Molecular Cloning: A Laboratory Manual*, Cold Spring Harbor, NY (1989), xi–xxxvii.
Ausubel et al. *Current Protocols in Molecular Biology*, Green Publishers Inc. & Wiley and Sons, NY (1994), iii–xi.
Engels et al., Gene Synthesis, *Angew. Chem. Intl. Ed.*, 28:716–734 (1989).
Miller et al., An Insect Baculovirus Host–Vector System For High–Level Expression of Foreign Genes, *Genetic Engineering*, 8: 277–298 (1986).
Ausubel et al., *Current Protocols in Molecular Biology*, Section 10.11.8, John Wiley and Sons, NY (1995), 10.11.8–10.11.22.
Marston et al., Solubilization of Protein Aggregates, *Meth. Enz*, 182: 264–275 (1990).
Merrifield, Solid Phase Peptide Synthesis, *Journal of American Chemical Society*, 85: 2149–2154 (1963).
Houghten, General method for the rapid solid–phase synthesis of large numbers of peptides: Specificity of antigen–antibody interaction at the level of individual amino acids, *Proc. Natl Acad. Sci. USA*, 82: 5131, (1985).

(List continued on next page.)

*Primary Examiner*—John Ulm
*Assistant Examiner*—Sally P. Teng
*Attorney, Agent, or Firm*—Nancy A. Oleski; Ron K. Levy; Steven M. Odre

[57] ABSTRACT

Disclosed is a novel gene termed ART which is expressed primarily in selected regions of the brain, as well as adrenal and lung tissues. Polypeptides encoded by ART are also disclosed, as are methods for preparing ART DNA and amino acid sequences.

26 Claims, 11 Drawing Sheets

OTHER PUBLICATIONS

Stewart and Young, *Solid Phase Peptide Synthesis*, Pierce Chemical Co., Rockford, IL, 1984, vii–xi.

Francis, protein modification and fusion proteins, *Focus on Growth Factors* 3: 4–10 (1992).

Chamow et al., Modification of CD4 Immunoadhesin with Monomethoxyply (ehtylene glycol) Aldehyde via Reductive Alkylation, *Bioconjugate Chem.*, 5: 133–140 (1994).

Remington's, *Pharmaceutical Sciences*, 18th edition, A.R. Gennaro, ed., Mack Publishing Company (1990), xv–xvi.

Sidman et al., Controlled release of macromolecules and pharmaceuticals form synthetic poly peptides based on glutamic acid, *Biopolymers*, 22: 547–556 (1983).

Langer et al., Biocompatibility of polymeric delivery systems for macromolecules, *J. Biomed. Mater. Res.*, 15: 167–277 (1981).

Langer, Controlled release of macromolecules, *Chem. Tech.*, 12: 98–105 (1982).

Eppstein et al., Biological activity of liposome–encapsulated murine interferon γ is mediated by a cell membrane receptor, *Proc. Natl. Acad. Sci. USA*, 82: 3688–3692 (1985).

Hwang et al., Hepatic uptake and degradation of unilamellar sphingomyelin/cholesterol lipsomes: A kinetic study, *Proc. Natl. Acad. Sci. USA*, 77: 4030–4034 (1980).

Gribskov et al., Profile Analysis: Detection of Distantly Related Proteins, *Proc. Natl. Acad. Sci. USA*, 84: 4355 (1987).

Luethy et al., Improving the Sensitivity of the Sequence Profile Method, *Protein Science*, 3: 139–146 (1994).

Hillier, L. et al. (Oct. 11, 1995) Washu–Merck EST Project. GenBank. EST–STS, EST–STS–Two. Accession No. H63735, Oct. 1995.

Hiller, L. et al., (Oct. 11, 1995) Washu–Merck EST Project. GenBank. EST–STS, EST–STS–Two, Accession No. H63298, Oct. 1995.

FIG. 1A

| | | | | | |
|---|---|---|---|---|---|
| GAATTCTTGG | AAGCACAGGA | AACAACATGC | CACATAGGGG | TTGAGTAAGC | ATCTCTGGGG | 60 |
| CCACAAATTA | AATTAAGCTT | TCAGGGCCGC | CTGCCTTGTT | ATTGCTAATG | GTTCTAGCCC | 120 |
| TGCTCAGCTC | CTAGGTCCCT | GTCCTGTGGA | AATTTGTGGA | CCCTGGGCAC | CCTCTCTTGC | 180 |
| TCCCAAATTT | TAATCGGCTC | CTGGAAACCT | CACCCCAAAT | TGGAGATAGG | CACTCCTCTT | 240 |
| GTAGAACAAA | AGGCTCAGGT | TCAGGGAGTG | AGGGCCTGAA | CTGTGCCCCC | ACCCTCCAGG | 300 |
| AAGGGTCCTT | CACGGCCTGG | CTGCAGGGAT | CAGTCACGTG | TGGCCCTTCA | TTAGGCCCTG | 360 |
| CCATATAAGC | CAAGGGCACG | GGGTGGCCGG | GAACTCTCTA | GGCAAGAATC | CCGGAGGCAG | 420 |
| AGGTGAGTCC | TCAGGTTGGG | CAGGGACTCC | TCCTCTCTGT | GGGGTCTCTA | TCTGGGCACC | 480 |
| TAGAGGGGAC | TCCAAGGATA | AGGAGGGACT | AAGTGGTACA | TCTTCCTGCT | GAGCCAGGCC | 540 |
| ATGCTGACCG | CAGCGGTGCT | GAGCTGTGCC | CTGCTGCTGG | CACTGCCTGC | CACGCGAGGA | 600 |
| GCCCAGATGG | GCTTGGCCCC | CATGGAGGGC | ATCAGAAGGC | CTGACCAGGC | CCTGCTCCCA | 660 |
| GAGCTCCCAG | GTCAGTGTGA | GCAAGGGTGG | GACTGGGCGG | GGCCTGAATA | CCCTCTGGCC | 720 |
| ACAAATAGTC | TCCCCTGGCA | TAAACCCTCT | TTCTCCCTTC | CAAACCCTC | CCTGGGAGG | 780 |
| TGGGTGCTTT | GTGCATGGGG | GTTCCTGCCC | TCACATCCTC | TGCCCCAGGC | CTGGGCCTGC | 840 |
| GGGCCCCACT | GAAGAAGACA | ACTGCAGAAC | AGGCAGAAGA | GGATCTGTTG | CAGGAGGCTC | 900 |
| AGGCCTTGGC | AGAGGTAACT | GCTCAGGGAA | AAGGGTAAGG | TGGTGGCCCT | TGGGAGGGGG | 960 |
| CATTGGGTAT | TAGCTCCTCT | CCCCAGCTCC | AAACTCCCTC | ACCAGCGACG | ACACTACCGA | 1020 |
| CCACCCCTTC | CCATGCTCCA | CTGCCATCCT | GCACAGGTTG | GGACAGGTAA | GATCCCTGGA | 1080 |
| TCTGTCTTTA | GAGGCCTGTG | CTGGTTCCCC | ACCCTGCAG | GTACTAGACC | TGCAGGACCG | 1140 |
| CGAGCCCCGC | TCCTCACGTC | GCTGCGTAAG | GCTGCATGAG | TCCTGCCTGG | GACAGCAGGT | 1200 |
| GCCTTGCTGT | GACCCATGTG | CCACGTGCTA | CTGCCGCTTC | TTCAATGCCT | TCTGCTACTG | 1260 |
| CCGCAAGCTG | GGTACTGCCA | TGAATCCCTG | CAGCCGCACC | TAGCTGGCCA | ACGTCAGGGT | 1320 |
| CGGGGCTAGG | GTAGGGGCAA | GGAAACTCGA | ATAAAGGATG | GGACCAACCC | CAAGGCTGTG | 1380 |
| GTTATTTCAA | ACGTGGCCGT | CAAAGGAGGG | AGGGTTCATG | GAGGGGGTGG | GAGTGTCACC | 1440 |
| AAGCCAAGAA | ACCACACATA | CTCTTATCCC | AGGGCCTGGG | CTACCCTATC | ATAGGAGGCA | 1500 |
| CATACACGGG | CGCTTTTAGG | GGTCCTGGTG | CCCCTGGGAA | AAATAGAGAA | GAGCCGCACT | 1560 |
| CCAGCTTTCG | AAAATCTTGT | ACAGCAAGTG | CGGGGAACGC | AGGACGCAGC | GTGGCACAGG | 1620 |

FIG.1B

```
GGCTATCACT CCTGGCTAAC AAATAAGCCT TAGGCTCCAG GGCTTGCTGC TACTTCCACG   1680
CAAAGCCTGC CCCTCATCCT GTTACCAGAG GGAAGGCCAG GAGTGTGCGT TGTTCAGGTC   1740
CTTAGCGTTT CGAACAAAGA ATTGAACAAA ACCCAGAAAG TAACAAACGA ATGACACACA   1800
GGAAGGAAGC AGACAGCTGG GATTGTTAA AGCGAGAAAG CACTACGCAG GGTGGGAGTG    1860
GGCCTGAGCA AGAGGCTGAA GGGGCTCAGT TACAAAGTTT TCCGGGTTTT AAGTACTCCT   1920
TTTGCCGGTCC CCCCTTATCT GGATGAAGGG TTTGGTCCAT GGCTAATTAA             1980
TCCATTTATG CCTGAGGGTTG CAATCTTTTT GAATTTTTGC AATCAGACCT TGGCCATGAC   2040
CTTGAGCAGT AGGATATAAA TAACTCCCAT ATGCTTAGCG TTCCAATAAT GGAACACAAG   2100
GCATAAATGG GGCTAAGGTG AATTGGCGCC CTATGCAGAT GAAGGGATGG CCCGTGCTTG   2160
GCCCGCAGCC AATCCAAGGC ACTCTCCCTT TCAACTGAGA CGTGGTGGAA GGGGAGGGT    2220
TGTGGGGACA GTGGCCTTTG ATCCTTTGTT ACTTGGACAT GGGGAGATGG GGTTTTCTT    2280
TTTGGTTTAG CTTTAGTAAG CTCGCCTTAG TTGGCCTCCG GTTCCCTGCC CCCAGACCTT   2340
GGTGTTTTCC CTTGATTCAG CTTCAGAATT C                                 2371
```

FIG.2

```
GGGCCCTCTA GATGCATGCT CGAGCGGCCG CCAGTGTGAT GGATATCTGC AGAATTCGGC     60
TTGGTCCCTG TCCTGTGGAA ATTTGTGGAC CCTGGGCACC CTCTCTTGCT CCCAAATTTT    120
AATCGGCTCC TGGAAACCTC ACCCCAAATT GGAGATAGGC ACTCCTCTTG TAGAACAAAA    180
GGCTCAGGTT CAGGGAGTGA GGGCCTGAAC TGTGCCCCCA CCCTCCAGGA AGGGTCCTTC    240
ACGGCCTGGC TGCAGGGATC AGTCACGTGT GGCCCTTCAT TAGGCCCTGC CATATAAGCC    300
AAAGGCACGG GGTGGCCCGG AACTCTCTAG GCAAGAATCC CGGAGGCAGA GGCCATGCTG    360
ACCGCAGCGG TGCTGAGCTG TGCCCTGCTG CTGGCACTGC CTGCCACGCG AGGAGCCCAG    420
ATGGGCTTGG CCCCCATGGA GGGCATCAGA AGGCCTGACC AGGCCCTGCT CCCAGAGCTC    480
CCAGGCCTGG GCCTGCGGGC CCCACTGAAG AAGACAACTG CAGAACAGGC AGAAGAGGAT    540
CTGTTGCAGG AGGCTCAGGC GTACTAGACC TGCAGGACCG TGCAGGACCG CGAGCCCCGC    600
TCCTCACGTC GCTGCGTAAG GCTGCATGAG TCCTGCCTGG GACAGCAGGT GCCTTGCTGT    660
GACCCATGTG CCACGTGCTA CTGCCCGCTT CTTCAATGCCT TCTGCTACTG CCGCAAGCTG    720
GGTACTGCCA TGAATCCCTG CAGCCGCACC TAGCTGGCCA ACGTCAGGAA GCCGAATTCC    780
AGCACACTGG CGGCCGTTAC TAGTGGATCC                                     810
```

FIG.3

```
GCCATGCTGA CCGCAGCGGT GCTGAGCTGT GCCCTGCTGC TGGCACTGCC TGCCACGCGA    60
GGAGCCCAGA TGGGCTTGGC CCCCATGGAG GGCATCAGAA GGCCTGACCA GGCCCTGCTC   120
CCAGAGCTCC CAGGCCTGGG CCTGCGGGCC CCACTGAAGA AGACAACTGC AGAACAGGCA   180
GAAGAGGATC TGTTGCAGGA GGCTCAGGCC TTGGCAGAGG TACTAGACCT GCAGGACCGC   240
GAGCCCCGCT CCTCACGTCG CTGCGTAAGG CTGCATGAGT CCTGCCTGGG ACAGCAGGTG   300
CCTTGCTGTG ACCCATGTGC CACGTGCTAC TGCCGCTTCT TCAATGCCTT CTGCTACTGC   360
CGCAAGCTGG GTACTGCCAT GAATCCCTGC AGCCGCACCT AGCTGGCCAA CGTCAGGAAG   420
CCGAATTCCA GCACACTGGC GGCCGTTACT AGTGGATCC                          459
```

FIG.4

```
Met Leu Thr Ala Ala Val Leu Ser Cys Ala Leu Leu Leu Ala Leu Pro
 1                   5                  10                  15

Ala Thr Arg Gly Ala Gln Met Gly Leu Ala Pro Met Glu Gly Ile Arg
                    20                  25                  30

Arg Pro Asp Gln Ala Leu Leu Pro Glu Leu Pro Gly Leu Gly Leu Arg
                    35                  40                  45

Ala Pro Leu Lys Lys Thr Thr Ala Glu Gln Ala Glu Glu Asp Leu Leu
            50                  55                  60

Gln Glu Ala Gln Ala Leu Ala Glu Val Leu Asp Leu Gln Asp Arg Glu
        65                  70                  75                  80

Pro Arg Ser Ser Arg Arg Cys Val Arg Leu His Glu Ser Cys Leu Gly
                    85                  90                  95

Gln Gln Val Pro Cys Cys Asp Pro Cys Ala Thr Cys Tyr Cys Arg Phe
                    100                 105                 110

Phe Asn Ala Phe Cys Tyr Cys Arg Lys Leu Gly Thr Ala Met Asn Pro
                115                 120                 125

Cys Ser Arg Thr
            130
```

FIG.5

```
Arg Glu Pro Arg Ser Ser Arg Arg Cys Val Arg Leu His Glu Ser Cys
 1               5                   10                      15
Leu Gly Gln Gln Val Pro Cys Cys Asp Pro Cys Ala Thr Cys Tyr Cys
                20                  25                      30
Arg Phe Phe Asn Ala Phe Cys Tyr Cys Arg Lys Leu Gly Thr Ala Met
                35                  40                      45
Asn Pro Cys Ser Arg Thr
 50
```

FIG.7

```
ATGCTGACTG CAATGTTGCT GAGTTGTGTT CTGCTGTTGG CACTGCCTCC CACACTGGGG    60
GTCCAGATGG GCGTGGCTCC ACTGAAGGGC ATCAGAAGGC CTGACCAGGC TCTGTTCCCA   120
GAGTTCCCAG GTGAGTATGG TCAGGTTGGG GATATGTGGG GCAACGACCA TTGCTGGCCA   180
CAGACCTGCC CGCCCAGGCT TAGACCTCCT TCCCCAATCC CAATCCCAAC CTAGGGAGGT   240
GGGTACTTGG TGCATGGTGG GTGTGGCCCT CACATCTTCT GCCCCAGGTC TAAGTCTGAA   300
TGGCCTCAAG AAGACAACTG CAGACCGAGC AGAAGAAGTT CTGCTGCAGA AGGCAGAAGC   360
TTTGGCGGAG GTAACTCATT AGGGAAAGGG ATAAAGTAGA AGGTAGGGCG CATCAGATAC   420
CATCATCTCT CCCCACTTCC GGATTACCCA ACCTGGGCAG AACTGCAGCC CCTCCCTGAC   480
CTCAGTCCAC TGCCACCCTA CTGGGGTCGG GGTTTGAGAG GCGAGTCTCG TTTCCTGAAC   540
TACGAATGCA GGTGCTAGAT CCACAGAACC GCGAGTCTCG TTCTCCGCGT CGCTGTGTAA   600
GGCTGCACGA GTCCTGCTTG GGACAGCAGG TACCTTGCTG CGACCCGTGC GCTACGTGCT   660
ACTGCCGCTT CTTCAATGCC TTTTGCTACT GCCGCAAGCT GGGTACGGCC ACGAACCTCT   720
GTAGTCGCAC CTAG                                                    734
```

FIG.8

```
Met Leu Thr Ala Met Leu Leu Ser Cys Val Leu Leu Leu Ala Leu Pro
 1               5                  10                  15

Pro Thr Leu Gly Val Gln Met Gly Val Ala Pro Leu Lys Gly Ile Arg
                20                  25                  30

Arg Pro Asp Gln Ala Leu Phe Pro Glu Phe Pro Gly Leu Ser Leu Asn
                35                  40                  45

Gly Leu Lys Lys Thr Thr Ala Asp Arg Ala Glu Glu Val Leu Leu Gln
                50                  55                  60

Lys Ala Glu Ala Leu Ala Glu Val Leu Asp Pro Gln Asn Arg Glu Ser
 65                 70                  75                  80

Arg Ser Pro Arg Arg Cys Val Arg Leu His Glu Ser Cys Leu Gly Gln
                85                  90                  95

Gln Val Pro Cys Cys Asp Pro Cys Ala Thr Cys Tyr Cys Arg Phe Phe
                100                 105                 110

Asn Ala Phe Cys Tyr Cys Arg Lys Leu Gly Thr Ala Thr Asn Leu Cys
                115                 120                 125

Ser Arg Thr
       130
```

FIG.9

```
Met Leu Thr Ala Ala Val Leu Ser Cys Ala Leu Leu Leu Ala Leu Pro
 1               5                  10                  15
Ala Thr Arg Gly Ala Gln Met Gly Leu Ala Pro Met Glu Gly Ile Arg
            20                  25                  30
Arg Pro Asp Gln Ala Leu Leu Pro Glu Leu Pro Gly Pro Gly Leu Arg
        35                  40                  45
Ala Pro Leu Lys Lys Thr Thr Ala Gln Ala Glu Glu Asp Leu Leu Leu
    50                  55                  60
Gln Glu Ala Gln Ala Leu Ala Glu Val Leu Asp Leu Gln Asp Arg Glu
65                  70                  75                  80
Pro Arg Ser Ser Arg Arg Cys Val Arg Leu His Glu Ser Cys Leu Gly
                85                  90                  95
Gln Gln Val Pro Cys Cys Asp Pro Cys Ala Thr Cys Tyr Cys Arg Phe
            100                 105                 110
Phe Asn Ala Phe Cys Tyr Cys Arg Lys Leu Gly Thr Ala Met Asn Pro
        115                 120                 125
Cys Ser Arg Thr
        130
```

GENES ENCODING ART, AN AGOUTI-RELATED TRANSCRIPT

This application claims the benefit of U.S. Provisional application Ser. No. 60/017,505 filed 10 May 1996.

BACKGROUND

1. Field of the Invention

This invention relates to novel human gene sequences and proteins encoded by the gene sequences. More specifically, the invention concerns a novel gene, termed "ART" (Agouti Related Transcript), that is expressed in selected tissues, and increases food uptake.

2. Description of Related Art

1. Agouti Gene

The agouti gene is present in most mammals, although its function in mammals other than rodents is unclear. The agouti gene product regulates the relative production of black or yellow pigment in the hair of many animals, including mice, squirrels, and wolves (A. G Searle, *Comparative Genetics of Coat Color in Mammals*, Academic Press, New York. N.Y. [1968]).

The mouse agouti gene has been cloned and sequenced (Bultman et al., *Cell*, 71:1195–1204 [1992]), and it encodes a 131 amino acid protein that is secreted. The agouti protein appears to act as an antagonist to the melanocortin-1 receptor ("MC1r") which is expressed on melanocytes (see Takeuchi, *J. Invest. Dermatol.*, 92:239S–242S [1989]; Jackson, *Nature*, 362:587–588 [1993]). MC1r, when occupied by melanocyte stimulating hormone (a-MSH), causes the melanocyte to synthesize black pigment (see Jackson, supra), and therefore, it appears that agouti blocks the action of a-MSH, thereby resulting in hairs with yellow pigment (Lu et al., *Nature*, 371:799–802 [1994]).

Similarly, Willard et al. (*Biochemistry*, 34:12341–12346 [1995]) have shown that partially purified mouse agouti protein acts as a potent antagonist of a-MSH at the MC1 receptor in B16F10 mouse melanoma cell cultures. Proteolytic cleavage of agouti protein at amino acid 83 generates a C-terminal fragment that is comparable in activity to full length agouti protein, suggesting that the active domain of agouti protein lies within its C-terminus (Willard et al., supra). This C-terminal fragment has 10 cysteines (the full length molecule has 11 cysteines).

In humans, the agouti gene is expressed in skin, heart, testes, ovary, and adipose tissue. This diverse tissue expression suggests that agouti may be involved in physiological processes other than pigmentation production (Wilson et al., *Human Mol. Gen.*, 4:233–230 [1995]; Kwon et al., *Proc. Natl. Acad. Sci USA*, 91:9760–9764 [1994]).

Several dominant phenotypes that result from agouti over-expression in transgenic mice have been identified. These include, for example, obesity, hyperinsulinemia, diabetes, and increased tumor susceptibility (see Manne et al., *Proc. Natl. Acad. Sci USA*, 92:4721–4724 [1995]). The degree and time of onset of obesity and hyperinsulinemia appear to be related to the level of agouti gene expression (Manne et al., supra). Further, these phenotypes do not seem to be related to the excess production of yellow pigment, since mice which have an inactive MC1 receptor show the same phenotype.

Mutant mice that over-express the agouti gene product have increased levels of intracellular calcium in the skeletal muscle (Zemel et al., *Proc. Natl. Acad. Sci USA*, 92:4728–4732 [1995]). Although the mechanism by which agouti produces this effect is not known, it does not appear to result either from release of intracellular stores of calcium or from a decreased efflux rate of calcium. Since skeletal muscle is important in the uptake of insulin, and this process is regulated at least in part by calcium levels, this increased intracellular calcium may explain in part the hyperinsulinemia observed in agouti mutant mice.

Interestingly, mouse agouti shares some amino acid sequence homology with certain spider and snail toxins that target specific neurotransmitter receptors or ion channels (Manne et al., supra; Ichida et al., *Neurochem. Res.*, 18:1137–1144 [1993]; Figueiredo et al., *Toxicon*, 33:83–93 [1995]). This homology is primarily confined to the C-terminus of the agouti protein, where the toxins and agouti share 8 cysteine residues. In the toxins, these cysteine residues form 4 disulfide bonds that are critical for toxin activity. Structural activity relationships using 3-dimensional NMR predicts that the disulfide bonds are required to form the tertiary structure needed to block calcium channels (Kim et al., *J. Mol. Biol.*, 250:659–671 [1995]).

In view of the amino acid sequence homologies of agouti with the spider and snail toxins, and the results obtained from mutant mice that over-express agouti, it has been suggested that agouti may be a member of a new class of molecules that regulate the activity of melanocortin receptors or certain types of calcium channel proteins (Manne et al., supra).

2. Melanocortin Receptors

In humans, there are currently five known melanocortin receptors and they are known as MC1r–MC5r. Two of these, MC1r and MC2r, show relative specificity for the ligands a-MSH and ACTH, respectively. MC1r and MC2r are expressed in melanocytes and the adrenal gland, respectively (Mountjoy et al., *Science*, 257:1248–1251 [1992]). MC3r is expressed in specific brain regions, while MC4r is expressed more widely throughout the brain, and MC5r is expressed in numerous peripheral tissues (Roselli-Reyfuss et al., *Proc. Natl. Acad. Sci. USA*, 90:8856–8860 [1993]; Mountjoy et al., *Science*, supra; Labbe et al., *Biochemistry*, 33:4543–4549 [1994]). The ligands and biological functions of MC3r, MC4r, and MC5r are presently unknown.

A role for melanocortin receptors in the central control of obesity has recently been suggested by the observation that injection of melanin concentrating hormone (MCH) into the brain of rats stimulates a feeding response (Qu et al., *Nature*, 380:243–247 [1996]). Although MCH does not have amino acid sequence homology with agouti, antibodies against MCH also recognize epitopes on agouti, and MCH also displays antagonistic activity at the MC1 receptor.

In view of the variety of physiological disorders and diseases (obesity, insulinemia, diabetes) that agouti and MCH have been implicated in, and in view of the fact that agouti and MCH antagonize MC receptors, there is a need in the art to identify and analyze related genes and proteins that may be involved in these same disorders.

Accordingly, it is an object to provide a compound that can modulate, either directly or indirectly, melanocortin receptor signaling, intra-cellular calcium levels, and/or body fat composition (such as adipose tissue level and/or distribution, circulating glucose levels, and/or insulin levels).

It is a further object to provide a compound that can increase food uptake.

These and other objectives will readily be apparent to one of ordinary skill in the art.

SUMMARY OF THE INVENTION

In one embodiment, the invention provides a nucleic acid molecule encoding a polypeptide selected from the group

3 consisting of: a nucleic acid molecule encoding a polypeptide selected from the group consisting of:

(a) the nucleic acid molecule of SEQ ID NO:4;

(b) the nucleic acid molecule of SEQ ID NO:5;

(c) the nucleic acid molecule of SEQ ID NO:6;

(d) the nucleic acid molecule of SEQ ID NO:9

(e) a nucleic acid molecule encoding the polypeptide of SEQ ID NO:8;

(f) a nucleic acid molecule encoding the polypeptide of SEQ ID NO:10;

(g) a nucleic acid molecule encoding the polypeptide of SEQ ID NO:11;

(h) a nucleic acid molecule that encodes a polypeptide that is at least 70 percent identical to the polypeptides of SEQ ID NO:7, SEQ ID NO:8, SEQ ID NO:10, SEQ ID NO:11; and (i) a nucleic acid molecule that is the complement of any of (a)–(h) above.

In another embodiment, the invention provides a vector comprising a nucleic acid molecule selected from the group set forth above, and a host cell comprising the vector.

In yet another embodiment, the invention provides a process for producing an ART polypeptide comprising the steps of:

(a) expressing a polypeptide encoded by a nucleic acid selected from the group set forth above, wherein the nucleic acid has been inserted into a suitable host; and (b) isolating the polypeptide.

The invention further provides an ART polypeptide selected from the group consisting of:

(a) the polypeptide of SEQ ID NO:7;

(b) the polypeptide of SEQ ID NO:8;

(c) the polypeptide of SEQ ID NO:10;

(d) the polypeptide of SEQ ID NO:11; and (e) a polypeptide that is 70 percent homologous with the polypeptide of (a) or (b), wherein the ART polypeptide may or may not possess an amino terminal methionine.

In one further embodiment, the invention provides a method of increasing food uptake in a mammal comprising administering an ART polypeptide to the mammal.

BRIEF DESCRIPTION OF THE DRAWINGS

FIGS. 1A and B depict the genomic DNA sequence of human ART (SEQ ID NO:4).

FIG. 2 depicts the ART cDNA from human brain tissue (SEQ ID NO:5).

FIG. 3 depicts the ART cDNA from human peripheral tissues (SEQ ID NO:6).

FIG. 4 depicts the full length translated amino acid sequence of human ART cDNA (SEQ ID NO:7).

FIG. 5 depicts a truncated human ART polypeptide (SEQ ID NO:8).

FIG. 7 depicts the mouse genomic DNA starting with exon 2 (the first coding exon) and also contains exons 3 and 4, as well as the corresponding introns (SEQ ID NO:9).

FIG. 8 depicts the full length translated amino acid sequence of mouse ART cDNA (SEQ ID NO:10).

FIG. 9 depicts the amino acid sequence of a human ART gene polymorphism. As is apparent, the amino acid at

4 position 45 (Leu in FIG. 4) is Pro in this polymorphic sequence (SEQ ID NO:11).

Figure 10:
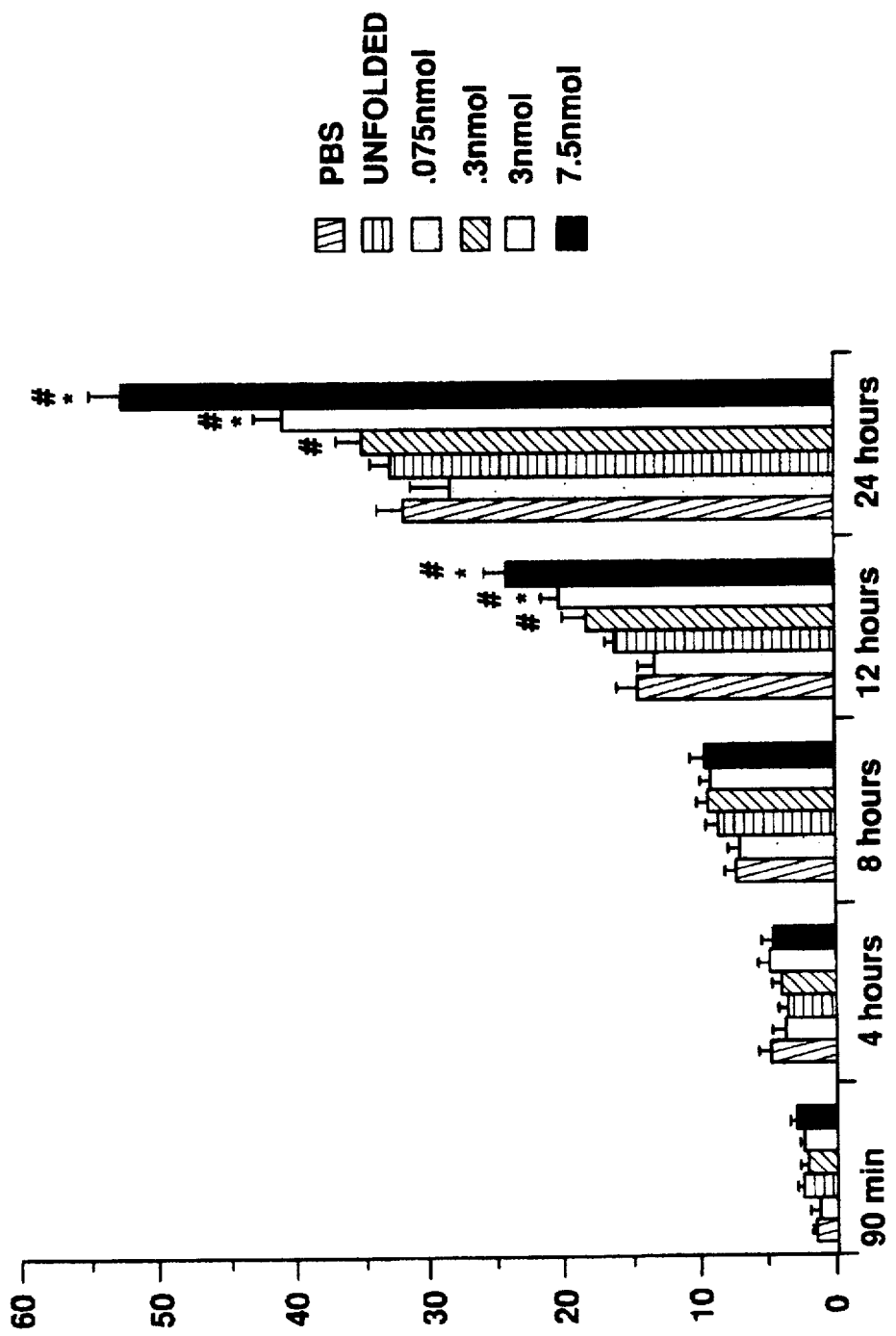

FIG. 10 is a graph of the feeding behavior pattern of rats injected with human ART polypeptide. The X axis represents the time after injection of ART at which food intake was measured; the Y axis represents the cumulative amount of food consumed in grams. Rats were injected with either PBS alone (control), "unfolded" ART (control), 0.075, 0.3, 3.0, or 7.5 nmol of folded ART in about a 2 μl volume. Standard error bars are indicated. Statistical analysis of the data where appropriate is indicated as: *=ps<0.006–0.0001 vs PBS, and #=ps<0.01–0.0001 vs unfolded ART.

DETAILED DESCRIPTION OF THE INVENTION

As used herein, the term "ART" when used to describe a nucleic acid molecule refers to a nucleic acid molecule or fragment thereof that (a) has the nucleotide sequence as set forth in SEQ ID NO: 4, SEQ ID NO:5, or SEQ ID NO:6; (b) has a nucleic acid sequence encoding a polypeptide that is at least 70 percent identical, preferably at least 80 percent identical, and more preferably at least 90 percent identical to the polypeptide encoded by any of SEQ ID NOS:4, 5, or 6; (c) is a naturally occurring allelic variant of (a) or (b); (d) is a nucleic acid variant of (a)–(c) produced as provided for herein; and/or (e) is complementary to (a)–(d).

Percent sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a predetermined portion of one or both sequences). The programs provide a "default" opening penalty and a "default" gap penalty, and a scoring matrix such as PAM 250 (a standard scoring matrix; see Dayhoff et al., in: *Atlas of Protein Sequence and Structure*, vol. 5, supp.3 [1978]) can be used in conjunction with the computer program. The percent identity can then be calculated as:

$$\frac{\text{Total number of identical matches}}{[\text{length of the longer sequence within the match span}] + [\text{number of gaps introduced into the longer sequence in order to align the two sequences}]} \times 100$$

Polypeptides that are at least 70 percent identical will typically have one or more amino acid substitutions, deletions, and/or insertions. Usually, the substitutions will be conservative so as to have little or no effect on the overall net charge, polarity, or hydrophobicity of the protein. Conservative substitutions are set forth in Table I below.

TABLE I

| Conservative amino acid substitutions | |
| --- | --- |
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |

TABLE I-continued

| Conservative amino acid substitutions | |
|---|---|
| | tyrosine |
| Small: | glycine |
| | alanine |
| | serine |
| | threonine |
| | methionine |

The term "stringent conditions" refers to hybridization and washing under conditions that permit only binding of a nucleic acid molecule such as an oligonucleotide or cDNA molecule probe to highly homologous sequences. One stringent wash solution is 0.015M NaCl, 0.005M NaCitrate, and 0.1 percent SDS used at a temperature of 55° C.–65° C. Another stringent wash solution is 0.2×SSC and 0.1 percent SDS used at a temperature of between 50° C.–65° C. Where oligonucleotide probes are used to screen cDNA or genomic libraries, the following stringent washing conditions may be used. One protocol uses 6×SSC with 0.05 percent sodium pyrophosphate at a temperature of 35° C.–62° C., depending on the length of the oligonucleotide probe. For example, 14 base pair probes are washed at 35°–40° C., 17 base pair probes are washed at 45°–50° C., 20 base pair probes are washed at 52°–57° C., and 23 base pair probes are washed at 57°–63° C. The temperature can be increased 2°–3° C. where the background non-specific binding appears high. A second protocol utilizes tetramethylammonium chloride (TMAC) for washing oligonucleotide probes. One stringent washing solution is 3M TMAC, 50 mM Tris-HCl, pH 8.0, and 0.2 percent SDS. The washing temperature using this solution is a function of the length of the probe. For example, a 17 base pair probe is washed at about 45°–50° C.

The term "ART protein" or "ART polypeptide" as used herein refers to any protein or polypeptide having the properties described herein for ART. The ART polypeptide may or may not have an amino terminal methionine, depending on the manner in which it is prepared. By way of illustration, ART protein or ART polypeptide includes, an amino acid sequence encoded by the nucleic acid molecule set forth in any of items (a)–(e) above and peptide or polypeptide fragments derived therefrom, to the amino acid sequence set forth in SEQ ID NOs:7 or 8, and/or to chemically modified derivatives as well as nucleic acid and or amino acid sequence variants thereof as provided for herein.

As used herein, the term "ART fragment" refers to a peptide or polypeptide that is less than the full length amino acid sequence of naturally occurring ART protein but has substantially the same biological activity as ART polypeptide or ART protein described above. Such a fragment may be truncated at the amino terminus, the carboxy terminus, and/or internally, and may be chemically modified. Preferably, the ART fragment will be a carboxy terminal fragment which retains at least all 10 C-terminal cysteine residues. Such ART fragments may be prepared with or without an amino terminal methionine. A preferred ART fragment is set forth in SEQ ID NO:8.

As used herein, the term "ART derivative" or "ART variant" refers to a ART polypeptide or ART protein that has 1) been chemically modified, as for example, by addition of polyethylene glycol or other compound, and/or 2) contains one or more nucleic acid or amino acid sequence substitutions, deletions, and/or insertions.

As used herein, the terms "biologically active polypeptide" and "biologically active fragment" refer to a peptide or polypeptide that has ART activity (i.e., is capable of modulating the signaling activity of a melanocortin receptor, is capable of modulating intracellular calcium levels, and/or is capable of modulating lipid metabolism).

As used herein, the terms "effective amount" and "therapeutically effective amount" refer to the amount of ART necessary to support one or more biological activities of ART as set forth above.

The ART polypeptides that have use in practicing the present invention may be naturally occurring full length polypeptides, or truncated polypeptides or peptides (i.e., "fragments"). The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring ART polypeptide (i.e., may contain one or more amino acid deletions, insertions, and/or substitutions as compared with naturally occurring ART).

The full length ART polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds. (*Current Protocols in Molecular Biology*, Green Publishers Inc. and Wiley and Sons, NY [1994]). A gene or cDNA encoding the ART protein or fragment thereof may be obtained for example by screening a genomic or cDNA library, or by PCR amplification. Alternatively, a gene encoding the ART polypeptide or fragment may be prepared by chemical synthesis using methods well known to the skilled artisan such as those described by Engels et al.(*Angew. Chem. Intl. Ed.*, 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the ART polypeptide will be several hundred nucleotides in length. Nucleic acids larger than about 100 nucleotides can be synthesized as several fragments using these methods. The fragments can then be ligated together to form the full length ART polypeptide. Usually, the DNA fragment encoding the amino terminus of the polypeptide will have an ATG, which encodes a methionine residue. This methionine may or may not be present on the mature form of the ART polypeptide, depending on whether the polypeptide produced in the host cell is secreted from that cell.

In some cases, it may be desirable to prepare nucleic acid and/or amino acid variants of naturally occurring ART. Nucleic acid variants (wherein one or more nucleotides are designed to differ from the wild-type or naturally occurring ART) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce ART. Other preferred variants are those encoding conservative amino acid changes (e.g., wherein the charge or polarity of the naturally occurring amino acid side chain is not altered substantially by substitution with a different amino acid) as compared to wild type, and/or those designed to either generate a novel glycosylation and/or phosphorylation site(s) on ART, or those designed to delete an existing glycosylation and/or phosphorylation site(s) on ART.

The ART gene or cDNA can be inserted into an appropriate expression vector for expression in a host cell. The vector is selected to be functional in the particular host cell employed (i.e., the vector is compatible with the host cell machinery such that amplification of the ART gene and/or expression of the gene can occur). The ART polypeptide or fragment thereof may be amplified/expressed in prokaryotic, yeast, insect (baculovirus systems) and/or eukaryotic host cells. Selection of the host cell will depend at least in part on whether the ART polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the ART polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the ART coding sequence that encodes polyHis (such as hexaHis) or another small immunogenic sequence. This tag will be expressed along with the protein, and can serve as an affinity tag for purification of the ART polypeptide from the host cell. Optionally, the tag can subsequently be removed from the purified ART polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native ART 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the ART 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the ART polypeptide. If the vector of choice does not contain an origin of replication site, one may be chemically synthesized based on a known sequence, and ligated into the vector.

The transcription termination element is typically located 3' to the end of the ART polypeptide coding sequence and serves to terminate transcription of the ART polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the ART polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for ART to be secreted from the host cell, a signal sequence may be used to direct the ART polypeptide out of the host cell where it is synthesized. Typically, the signal sequence is positioned in the coding region of ART nucleic acid sequence, or directly at the 5' end of the ART coding region. Many signal sequences have been identified, and any of them that are functional in the selected host cell may be used in conjunction with the ART gene. Therefore, the signal sequence may be homologous or heterologous to the ART polypeptide, and may be homologous or heterologous to the ART polypeptide. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the ART polypeptide is increased by the presence of one or more introns on the vector; this is particularly true for eukaryotic host cells, especially mammalian host cells. The intron may be naturally occurring within the ART nucleic acid sequence, especially where the ART sequence used is a full length genomic sequence or a fragment thereof. Where the intron is not naturally occurring within the ART DNA sequence (as for most cDNAs), the intron(s) may be obtained from another source. The position of the intron with respect to the 5' flanking sequence and the ART coding sequence is important, as the intron must be transcribed to be effective. As such, where the ART nucleic acid sequence is a cDNA sequence, the preferred position for the intron is 3' to the transcription start site, and 5' to the polyA transcription termination sequence. Preferably for ART cDNAs, the intron will be located on one side or the other (i.e., 5' or 3') of the ART coding sequence such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII (Invitrogen Company, San Diego, Calif.), pBSII (Stratagene Company, LaJolla, Calif.), and pETL (BlueBacII; Invitrogen).

After the vector has been constructed and a ART nucleic acid has been inserted into the proper site of the vector, the completed vector may be inserted into a suitable host cell for amplification and/or ART polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize ART protein which can subsequently be collected from the culture medium (if the host cell secretes it into the medium) or directly from the host cell producing it (if it is not secreted). After collection, the ART protein can be purified using methods such as molecular sieve chromatography, affinity chromatography, and the like.

Selection of the host cell will depend in part on whether the ART protein is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize biologically active ART, the ART may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α,DH10, and MC1061) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where desired, insect cells may be utilized as host cells in the method of the present invention (Miller et al., *Genetic Engineering* 8:277–298 [1986]).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of ART polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the ART polypeptide has been designed to be secreted from the host cells, the majority of polypeptide will likely be found in the cell culture medium. Polypeptides prepared in this way will typically not possess an amino terminal methionine, as it is removed during secretion from the cell. If however, the ART polypeptide is not secreted from the host cells, it will be present in the cytoplasm (for eukaryotic, gram positive bacteria, and insect host cells) or in the periplasm (for gram negative bacteria host cells) and may have an amino terminal methionine.

For intracellular ART protein, the host cells are typically first disrupted mechanically or osmotically to release the cytoplasmic contents into a buffered solution. ART polypeptide can then be isolated from this solution.

Purification of ART polypeptide from solution can be accomplished using a variety of techniques. If the polypeptide has been synthesized such that it contains a tag such as Hexahistidine (ART/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing ART). For example, polyhistidine binds with great affinity and specificity to nickel, thus an affinity column of nickel (such as the Qiagen nickel columns) can be used for purification of ART/polyHis. (See for example, Ausubel et al., eds., *Current Protocols in Molecular Biology*, Section 10.11.8, John Wiley & Sons, New York [1993]).

Where the ART polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

If it is anticipated that the ART polypeptide will be found primarily in the periplasmic space of the bacteria or the cytoplasm of eukaryotic cells, the contents of the periplasm or cytoplasm, including inclusion bodies (e.g., gram-negative bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the ART polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The ART polypeptide in its now soluble form can then be analyzed using gel electrophoresis, immunoprecipitation or the like. If it is desired to isolate the ART polypeptide, isolation may be accomplished using standard methods such as those set forth below and in Marston et al. (*Meth. Enz.*, 182:264–275 [1990]).

If ART polypeptide inclusion bodies are not formed to a significant degree in the periplasm of the host cell, the ART polypeptide will be found primarily in the supernatant after centrifugation of the cell homogenate, and the ART polypeptide can be isolated from the supernatant using methods such as those set forth below.

In those situations where it is preferable to partially or completely isolate the ART polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying ART polypeptide using recombinant DNA techniques, the ART polypeptides, fragments, and/or derivatives thereof may be prepared by chemical synthesis methods (such as solid phase peptide synthesis) using methods known in the art such as those set forth by Merrifield et al., (*J. Am. Chem. Soc.*, 85:2149 [1964]), Houghten et al. (*Proc Natl Acad. Sci. USA*, 82:5132 [1985]), and Stewart and Young (Solid Phase Peptide Synthesis, Pierce Chem Co, Rockford, Ill. [1984]). Such polypeptides may be synthesized with or without a methionine on the amino terminus. Chemically synthesized ART polypeptides or fragments may be oxidized using methods set forth in these references to form disulfide bridges. The ART polypeptides or fragments may be employed as biologically active or immunological substitutes for natural, purified ART polypeptides in therapeutic and immunological processes.

Chemically modified ART compositions (i.e., "derivatives") where the ART polypeptide is linked to a polymer ("ART-polymers") are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. A preferred reactive aldehyde is polyethylene glycol propionaldehyde, which is water stable, or mono C1–C10 alkoxy or aryloxy derivatives thereof (see U.S. Pat. No. 5,252,714). The polymer may be branched or unbranched. Included within the scope of ART-polymers is a mixture of polymers. Preferably, for therapeutic use of the end-product preparation, the polymer will be pharmaceutically acceptable. The water soluble polymer or mixture thereof may be selected from the group consisting of, for example, polyethylene glycol (PEG), monomethoxypolyethylene glycol, dextran, cellulose, or other carbohydrate based polymers, poly- (N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. For the acylation reactions, the polymer(s) selected should have a single reactive ester group. For reductive alkylation, the polymer(s) selected should have a single reactive aldehyde group. The polymer may be of any molecular weight, and may be branched or unbranched.

Pegylation of ART may be carried out by any of the pegylation reactions known in the art, as described for example in the following references: *Focus on Growth Factors* 3 (2): 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

Pegylation by acylation generally involves reacting an active ester derivative of polyethylene glycol (PEG) with an ART protein. Any known or subsequently discovered reactive PEG molecule may be used to carry out the pegylation of ART. A preferred activated PEG ester is PEG esterified to N-hydroxysuccinimide ("NHS"). As used herein, "acylation" is contemplated to include without limitation the following types of linkages between ART and a water soluble polymer such as PEG: amide, carbamate, urethane, and the like, as described in *Bioconjugate Chem.* 5:133–140 (1994). Reaction conditions may be selected from any of those known in the pegylation art or those subsequently developed, provided that conditions such as temperature, solvent, and pH that would inactivate the ART species to be modified are avoided.

Pegylation by acylation usually results in a polypegylated ART product, wherein the lysine $\epsilon$-amino groups are pegylated via an acyl linking group. Preferably, the connecting linkage will be an amide. Also preferably, the resulting product will be at least about 95 percent mono, di- or tri- pegylated. However, some species with higher degrees of pegylation (up to the maximum number of lysine $\epsilon$-amino acid groups of ART plus one $\alpha$-amino group at the amino terminus of ART) will normally be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with a protein such as ART in the presence of a reducing agent. Regardless of the degree of pegylation, the PEG groups are preferably attached to the protein via a $—CH_2—NH—$ group. With particular reference to the $—CH_2—$ group, this type of linkage is referred to herein as an "alkyl" linkage.

Derivatization via reductive alkylation to produce a monopegylated product exploits the differential reactivity of different types of primary amino groups (lysine versus the N-terminal) available for derivatization in ART. Typically, the reaction is performed at a pH (see below) which allows one to take advantage of the $pK_a$ differences between the $\epsilon$-amino groups of the lysine residues and that of the $\alpha$-amino group of the N-terminal residue of the protein. By such selective derivatization, attachment of a water soluble polymer that contains a reactive group such as an aldehyde, to a protein is controlled: the conjugation with the polymer occurs predominantly at the N-terminus of the protein without significant modification of other reactive groups such as the lysine side chain amino groups. The present invention provides for a substantially homogeneous preparation of ART-monopolymer protein conjugate molecules (meaning ART protein to which a polymer molecule has been attached substantially only (i.e., at least about 95%) in a single location on the ART protein. More specifically, if polyethylene glycol is used, the present invention also provides for pegylated ART protein lacking possibly antigenic linking groups, and having the polyethylene glycol molecule directly coupled to the ART protein.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable conditions used to react a biologically active substance with an activated polymer molecule. Methods for preparing pegylated ART will generally comprise the steps of (a) reacting an ART polypeptide with polyethylene glycol (such as a reactive ester or aldehyde derivative of PEG) under conditions whereby ART becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Reductive alkylation to produce a substantially homogeneous population of mono-polymer/ART protein conjugate molecule will generally comprise the steps of: (a) reacting a ART protein with a reactive PEG molecule under reductive alkylation conditions, at a pH suitable to permit selective modification of the $\alpha$-amino group at the amino terminus of said ART protein; and (b) obtaining the reaction product(s).

For a substantially homogeneous population of mono-polymer/ART protein conjugate molecules, the reductive alkylation reaction conditions are those which permit the selective attachment of the water soluble polymer moiety to the N-terminus of ART. Such reaction conditions generally provide for pKa differences between the lysine amino groups and the $\alpha$-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal $\alpha$-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa (the term "about" indicating ±30 kDa). The preferred average molecular weight is about 5 kDa to about 50 kDa, particularly preferably about 12 kDa to about 25 kDa. The ratio of water-soluble polymer to ART protein will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any ART protein having an α-amino group at the amino terminus, and provide for a substantially homogenous preparation of monopolymer/ART protein conjugate. The term "monopolymer/ART protein conjugate" is used here to mean a composition comprised of a single polymer molecule attached to an ART protein molecule. The monopolymer/ART protein conjugate preferably will have a polymer molecule located at the N-terminus, but not on lysine amino side groups. The preparation will preferably be greater than 90% monopolymer/ART protein conjugate, and more preferably greater than 95% monopolymer ART protein conjugate, with the remainder of observable molecules being unreacted (i.e., protein lacking the polymer moiety). The examples below provide for a preparation which is at least about 90% monopolymer/protein conjugate, and about 10% unreacted protein. The monopolymer/protein conjugate has biological activity.

For the present reductive alkylation, the reducing agent should be stable in aqueous solution and preferably be able to reduce only the Schiff base formed in the initial process of reductive alkylation. Preferred reducing agents may be selected from the group consisting of sodium borohydride, sodium cyanoborohydride, dimethylamine borane, trimethylamine borane and pyridine borane. A particularly preferred reducing agent is sodium cyanoborohydride.

Other reaction parameters, such as solvent, reaction times, temperatures, etc., and means of purification of products, can be determined based on the published information relating to derivatization of proteins with water soluble polymers.

A mixture of polymer-ART protein conjugate molecules may be prepared by acylation and/or alkylation methods, as described above,and one may select the proportion of monopolymer/protein conjugate to include in the mixture. Thus, where desired, a mixture of various protein with various numbers of polymer molecules attached (i.e., di-, tri-, tetra-, etc.) may be prepared and combined with the monopolymer/ART protein conjugate material prepared using the present methods.

Generally, conditions which may be alleviated or modulated by administration of the present polymer/ART include those described herein for ART molecules in general. However, the polymer/ART molecules disclosed herein may have additional activities, enhanced or reduced activities, or other characteristics, as compared to the non-derivatized molecules.

ART nucleic acid molecules, fragments, and/or derivatives that do not themselves encode polypeptides that are active in activity assays may be useful as hybridization probes in diagnostic assays to test, either qualitatively or quantitatively, for the presence of ART DNA or RNA in mammalian tissue or bodily fluid samples.

ART polypeptide fragments and/or derivatives that are not themselves active in activity assays may be useful as modulators (e.g., inhibitors or stimulants) of the ART receptors in vitro or in vivo, or to prepare antibodies to ART polypeptides.

The ART polypeptides and fragments thereof, whether or not chemically modified, may be employed alone, or in combination with other pharmaceutical compositions such as, for example, neurotrophic factors, cytokines, interferons, interleukins, growth factors, antibiotics, anti-inflammatories, neurotransmitter receptor agonists or antagonists and/or antibodies, in the treatment of endocrine system disorders.

The ART polypeptides and/or fragments thereof may be used to prepare antibodies generated by standard methods.

Thus, antibodies that react with the ART polypeptides, as well as reactive fragments of such antibodies, are also contemplated as within the scope of the present invention. The antibodies may be polyclonal, monoclonal, recombinant, chimeric, single-chain and/or bispecific, etc. The antibody fragments may be any fragment that is reactive with the ART of the present invention, such as, $F_{ab}$, $F_{ab'}$, etc. Also provided by this invention are the hybridomas generated by presenting ART or a fragment thereof as an antigen to a selected mammal, followed by fusing cells (e.g., spleen cells) of the animal with certain cancer cells to create immortalized cell lines by known techniques. The methods employed to generate such cell lines and antibodies directed against all or portions of a human ART polypeptide of the present invention are also encompassed by this invention.

The antibodies may be used therapeutically, such as to inhibit binding of the ART to its receptor. The antibodies may further be used for in vivo and in vitro diagnostic purposes, such as in labeled form to detect the presence of the ART in a body fluid.

Therapeutic Compositions and Administration

Therapeutic compositions for treating various endocrine and/or neuro-endocrine system disorders such as glucocorticoid resistance, Cushing's syndrome (either genetic or caued by ectopic ACTH production due to pituitary tumors, small lung carcinomas, or adrenal tumors), congenital adrenal hyperplasia, other disorders of the hypothalamic-pituitary axis (HPA), and/or obesity are within the scope of the present invention. Such compositions may comprise a therapeutically effective amount of a ART polypeptide or fragment thereof (either of which may be chemically modified) in admixture with a pharmaceutically acceptable carrier. The carrier material may be water for injection, preferably supplemented with other materials common in solutions for administration to mammals. Typically, a ART therapeutic compound will be administered in the form of a composition comprising purified protein (which may be chemically modified) in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

The ART compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of ART compositions useful for practicing the present invention may be prepared for storage by mixing the selected composition having the desired degree of purity with optional physiologically acceptable carriers, excipients, or stabilizers (*Remington's Pharmaceutical Sciences*, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The ART composition to be used for in vivo administration must be sterile. This is readily accomplished by filtration through sterile filtration membranes. Where the ART composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, ART may be administered locally via implantation into the affected area of a membrane, sponge, or other appropriate material on to which ART polypeptide has been absorbed.

Where an implantation device is used, the device may be implanted any suitable tissue or organ, such as, for example, into a cerebral ventricle or into brain parenchyma, and delivery of ART may be directly through the device via bolus or continuous administration, or via a catheter using continuous infusion.

ART polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers*, 22:547–556 [1983]), poly (2-hydroxyethyl-methacrylate) (Langer et al., *J. Biomed. Mater. Res.*, 15:167–277 [1981] and Langer, Chem. Tech., 12:98–105 [1982]), ethylene vinyl acetate (Langer et al., supra) or poly-D(−)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA*, 82:3688–3692 [1985]; Hwang et al., *Proc. Natl. Acad. Sci. USA*, 77:4030–4034 [1980]; EP 52,322; EP 36,676; EP 88,046; EP 143,949).

In some cases, it may be desirable to use ART compositions in an ex vivo manner, i.e., to treat cells or tissues that have been removed from the patient and are then subsequently implanted back into the patient.

In other cases, ART may be delivered through implanting into patients certain cells that have been genetically engineered (using methods described above) to express and secrete ART polypeptide. Such cells may be human cells, and may be derived from the patient's own tissue or from another source, either human or non-human. Optionally, the cells may be immortalized. The cells may be implanted into the brain, adrenal gland or into other body tissues or organs.

In certain situations, it may be desirable to use gene therapy methods for administration of ART to patients suffering from certain endocrine and/or neuro-endocrine system disorders or diseases such as glucocorticoid resistance, Cushing's syndrome (either genetic or caued by ectopic ACTH production due to pituitary tumors, small lung carcinomas, or adrenal tumors), congenital adrenal hyperplasia, other disorders of the hypothalamic-pituitary axis (HPA), and/or obesity. In these situations, genomic DNA, cDNA, and/or synthetic DNA encoding ART or a fragment or variant thereof may be operably linked to a constitutive or inducible promoter that is active in the tissue into which the composition will be injected. This ART DNA construct can be injected directly into brain or other neuronal tissue to be treated.

Alternatively, the ART DNA construct may be injected into muscle tissue where it can be taken up into the cells and expressed in the cells, provided that the ART DNA is operably linked to a promoter that is active in muscle tissue such as cytomegalovirus (CMV) promoter, Rous sarcoma virus (RSV) promoter, or muscle creatine kinase promoter. Typically, the DNA construct may include (in addition to the ART DNA and a promoter), vector sequence obtained from vectors such as adenovirus vector, adeno-associated virus vector, a retroviral vector, and/or a herpes virus vector. The vector/DNA construct may be admixed with a pharmaceutically acceptable carrier(s) for injection.

An effective amount of the ART composition(s) to be employed therapeutically will depend, for example, upon the therapeutic objectives such as the indication for which ART is being used, the route of administration, and the condition of the patient. Accordingly, it will be necessary for the therapist to titer the dosage and modify the route of administration as required to obtain the optimal therapeutic effect. A typical daily dosage may range from about 0.1 µg/kg to up to 100 mg/kg or more, depending on the factors mentioned above. Typically, a clinician will administer the ART composition until a dosage is reached that achieves the desired effect. The ART composition may therefore be administered as a single dose, or as two or more doses (which may or may not contain the same amount of ART) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing. Generally, the dosage will be between 0.01 µg/kg body weight (calculating the mass of the protein alone, without chemical modification) and 300 µg/kg (based on the same).

The ART proteins, fragments and/or derivatives thereof may be utilized to treat diseases and disorders of the endocrine system which may be associated with alterations in the pattern of ART expression or which may benefit from exposure to ART or anti-ART antibodies.

ART protein, and/or fragments or derivatives thereof, may be used to treat patients in whom various cells of the endocrine and/or nervous system have degenerated and/or have been damaged by congenital disease, trauma, surgery, stroke, ischemia, infection, metabolic disease, nutritional deficiency, malignancy, and/or toxic agents.

In other embodiments of the invention, ART protein and/or fragments or derivatives thereof can be used to treat endocrine and/or neuro-endocrine system disorders or diseases such as glucocorticoid resistance, Cushing's syndrome (either genetic or caued by ectopic ACTH production due to pituitary tumors, small lung carcinomas, or adrenal tumors), congenital adrenal hyperplasia, other disorders of the hypothalamic-pitutary axis (HPA), and/or obesity. In addition, ART compositions may be useful in modulating intra-cellular calcium levels.

In addition, ART protein or peptide fragments or derivatives thereof can be used in conjunction with surgical implantation of tissue in the treatment of diseases in which tissue implantation is indicated.

The following examples are intended for illustration purposes only, and should not be construed as limiting the scope of the invention in any way.

EXAMPLES

Example I:

Identification of Human ART cDNA

The publicly available Washington University/Merck DNA sequence database referred to as the EST (Expressed Sequence Tag) database was searched with a sequence profile (Gribskov et al., *Proc. Natl. Acad. Sci, USA*, 84:4355 [1987] and Luethy et al., *Protein Science*, 3:139–146 [1994]) using a sequence alignment of the human and mouse agouti genes (starting at amino acid 22 of both mouse and human agouti), along with the PAM250 amino acid substitution table (Dayhoff et al., in: *Atlas of Protein Sequence and Structure*, vol 5, supp. 3 [1978]).

In order to search the database for homologous amino acid sequences, each entry in the EST database was first translated by computer from DNA to amino acid sequence prior to searching. One EST database submission cDNA clone, H63735, was found to have homology to this profile sequence. The submission containing the sequence of the opposite end of this cDNA clone, H63298, was examined but did not show any homology to the profile sequence.

The *E. coli* stock containing the cDNA clone corresponding to H63735 and H63298 (stock number 208641) was obtained from Genome Systems Inc., St. Louis, Mo. The DNA from this clone was prepared using standard miniprep methods (Sambrook et al., *Molecular Cloning: A Laboratoy Manual*, Cold Spring Harbor Laboratory Press, Cold Spring Harbor, N.Y. [1989]). The DNA was purified by passage through a Qiagen column (Qiagen, Chatsworth, Calif.) and following the manufacturer's protocol. After purification, the DNA was sequenced using the standard dideoxy chain termination method. When this purified DNA was digested with the restriction endonucleases EcoRI and HindIII, two fragments of about 1.2 and 0.3 kb were obtained, indicating the clone contained an insert of approximately 1.5 kb. Sequence from the T3 and T7 primers of the sequencing vector yielded sequence which was nearly identical to the submitted sequences, indicating that clone 208641 contained the DNA used to generate submissions H63735 and H63298.

Analysis of the full cDNA sequence of clone 208641 confirmed the presence of homology with the agouti gene in the cysteine-rich carboxy terminus. Comparison of the cDNA sequence of clone 208641 with the original sequence submitted in the database (H63735) revealed an error in the submitted sequence. Specifically, an extra guanine nucleotide was present at position 164 of H63735, resulting in a frameshift mutation and a premature in-frame termination codon when H63735 was translated. This error, when corrected, revealed increased homology between the profile sequence and H63735. Correction of this error resulted in additional sequence homology between clone 208641 and the agouti gene as well. However, even with the correction of this frame shift, the predicted protein sequence of 208641 from the open reading frame resulted in a protein of 94 amino acids, compared to 132 amino acids for human agouti. In addition, the predicted protein homology decreased dramatically towards the amino terminus. This suggested that 208641 was actually not a genuine cDNA, but rather a partially spliced genomic intron DNA-cDNA hybrid, and this was confirmed when the sequence for the human genomic clone (SEQ ID NO:4) was obtained, as described below.

To assess the gene expression pattern of the clone, nylon Northern blots containing about 2 μg per lane of polyA RNA from various human tissues (Clontech Labs, Palo Alto, Calif.) were screened for the presence of ART by probing the blots with an approximately 600 base pair probe (obtained by digesting clone 208641 with NcoI and NotI and isolating the 600 base pair fragment using the Qiagen Gel Purification Kit [Qiagen, Chatsworth, Calif.]) and following the manufacturer's protocol. This isolated 600 bp fragment was radioactively labelled with a-$^{32}$P-dCTP using standard methods (RediVue, Amersham, Arlington Heights, Ill.) in a random primed reaction (RediPrime, Amersham). Unincorporated radioactivity was excluded by size exclusion chromatography (QuickSpin columns, Boehringer-Mannheim). The Northern filters were hybridized overnight at about 42° C. in buffer containing 50% formamide, 2% SDS, 10×Denhardts, 100 mg/ml salmon sperm DNA, and 5×SSPE. The filters were then washed in 2×SSC, 0.05% SDS at room temperature for about 40 minutes with three changes of wash solution, followed by 30 minutes at about 50° C. in 0.1×SSC, 0.1%SDS. Hybridization signals were detected by placing the filters in a phosphoimager cassette overnight.

Figure 6:
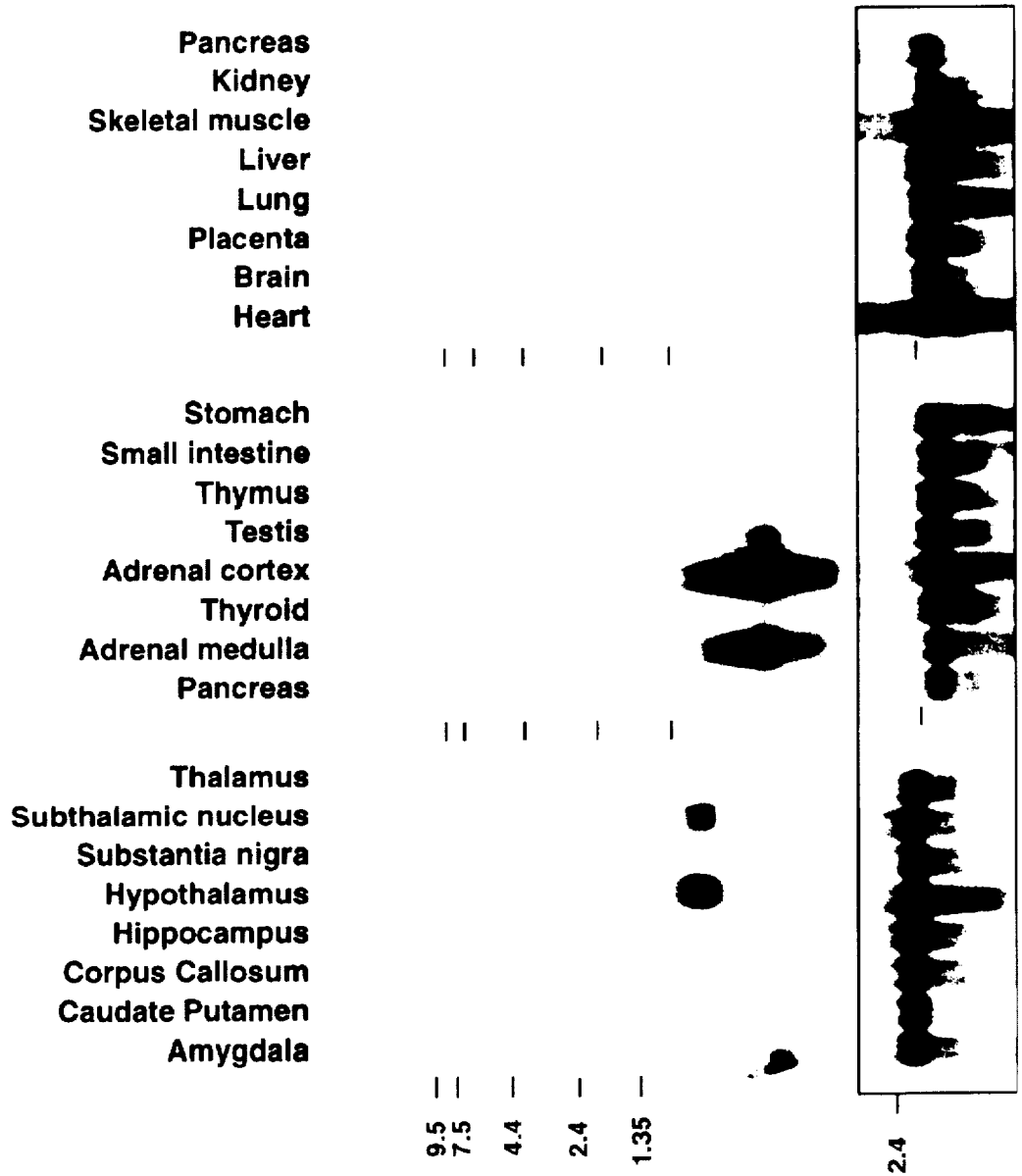
FIG. 6 depicts a Northern blot of various human tissues as indicated. The blot was probed with an ART cDNA as described in the Examples.

Hybridization of the Northern filters with the 600 bp NcoI-NotI probe revealed a striking and relatively specific pattern of expression of ART, as is shown in FIG. 6. The most abundant site of expression was the adrenal cortex, followed by the adrenal medulla, hypothalamus, subthalamic nucleus, and testis. A weak hybridization signal was detected in lung. When the relative intensities of the hybridization signals were quantitated on a phosphoimager and expressed relative to adrenal cortex, the following values were obtained; adrenal cortex, 100; adrenal medulla, 46; hypothalamus, 23; testis, 15; subthalamic nucleus, 11; and lung, 3.6. The filters were then probed with a beta-actin probe to verify equal loading of RNA and accurate placement of RNA size markers.

Examination of the Northern blot with reference to the size markers revealed an interesting difference in transcript length of ART between brain and peripheral tissues, which could be due to alternative exon splicing. The transcript size was approximately 0.8 kb for the brain tissues, while the peripheral tissues had a smaller transcript of approximately 0.5 kb. To resolve whether this represented the alternative splicing of coding and/or untranslated exons, the cDNA from both subthalamic nucleus and adrenal gland was cloned as described below.

Initial attempts to clone the full length cDNA using standard phage libraries were unsuccessful, which was most likely due to the small transcript size being excluded during the preparation of such libraries. Accordingly, a more sophisticated and technically challenging cloning method utilizing PCR was attempted. To obtain the full-length human cDNA clone corresponding to clone 208641, human polyA RNA from adrenal gland, subthalamic nucleus, and lung (Clontech, Palo Alto, Calif.; catalog numbers 6571-1, 6581-1, and 6524-1, respectively) was reverse transcribed, second strand cDNA was synthesized, and ligated to adaptor primers using the Marathon cDNA amplification kit (Clontech, Palo Alto, Calif.), following the manufacturer's protocol. The final cDNA products were purified from unligated adaptor primers (PCR Clean-up kit, Qiagen, Chatsworth, Calif.), and used as templates for subsequent RACE reactions using PCR. PCR was performed for each cDNA using the following primers:

CCATCCTAATACGACTCACTATAGGGC    (SEQ ID NO:1)

TAGCCCCGACCCTGACGTTGGC    (SEQ ID NO:2)

and using the Advantage PCR kit components (Clontech, Palo Alto, Calif.). Following an initial denaturation step (94° C. for 3 minutes), the reactions were cycled 5 times at 94° C. for 15 seconds and then 72° C. for 2 minutes; 5 times at 94° C. for 15 seconds and then 70° C. for 2 minutes; and 25 cycles at 94° C. for 15 seconds and then 68° C. for 2 minutes. All reactions were conducted on a Perkin Elmer 2400 PCR machine.

An aliquot of each PCR reaction mix was electrophoresed on an agarose gel, and the bands migrating at approximately 600 base pairs were excised and purified (Gel Extraction kit, Qiagen, Chatsworth, Calif.) and used as a template for subsequent PCR using the primer SEQ ID NO:2 and the primer:

ACTCACTATAGGGCTCGAGCGGC    (SEQ ID NO:3)

The PCR conditions were the same as described above.

An aliquot of this second PCR reaction was electrophoresed on agarose, and the bands migrating at approximately 600 base pairs were excised, purified, and cloned into a plasmid (TA Cloning kit, Invitrogen, San Diego, Calif.). Bacterial host cells were then transformed with the plasmid, and grown overnight for DNA purification. The plasmid DNA was then isolated from the bacteria host cells using the Qiagen miniprep protocol, digested with EcoRI, and electrophoresed to confirm the presence and size of the inserts. Clones containing a variety of insert sizes were sequenced using various T7 and M13 primers. Sequencing of the clones indicated a polymorphism in the second position of codon 135 corresponding to the predicted amino acids Leu (CTG) or Pro (CCG; see FIGS. 4 and 9). The sequences obtained were used to determine which clones had inserts that contained ART cDNA, and to design oligonucleotide primers to the 5' portion of the ART cDNA. When a number of these inserts were sequenced, only the larger insert sizes of 700 bp and 500 bp for the subthalamic nucleus and adrenal gland, respectively, contained ART transcripts. Both of these inserts contained the same open reading frame (ORF), but differed in the amount of 5' untranslated region. This ORF matched the seqence from 208641 in the 3' region.

For the 3' RACE reaction, an oligonucleotide on the forward strand that overlapped the 5' RACE product by about 180 bp was used with SEQ ID NO:1. This resulted in the same sized amplicon (about 300 bp) from all three tissues. The sequence from this amplicon was the same from all three tissues, and also matched the sequence from clone 208641. The sequence of the adrenal gland and lung ("peripheral tissues") ART cDNA is shown in FIG. 3 (SEQ ID NO:6).

The combined sequence from the subthalamic nucleus RACE reactions is shown in FIG. 2 (SEQ ID NO:5). As mentioned above, the sequence from the adrenal gland and lung was identical to this sequence except for the length of the 5' untranslated region. This cDNA sequence contains in-frame termination codons from the presumed translation start site, a polyadenylation signal, and a polyA tail. The protein predicted from this ORF contains 132 amino acids, a signal peptide sequence and 11 cysteines, and this sequence is shown in FIG. 4 (SEQ ID NO:7). The signal peptide consist of the first 20 amino acids, and the mature polypeptide starts at amino acid 21 (Ala).

Example II

Identification of Human ART Genomic DNA

High density filters spotted with DNA from human genomic DNA (obtained from Genome Systems Inc., St. Louis, Mo.) were hybridized with the 600 bp a-$^{32}$P-dCTP labelled NcoI-NotI cDNA probe (see Example I) in RapidHyb buffer (Amersham, Arlington Heights, Ill.; catalog number RPN 1636) at about 65° C. for about 4 hours. The filters were then washed in 2×SSC containing 0.2% SDS at room temperature for 30 minutes, and then in 0.2×SSC containing 0.2% SDS at 65° C. for 30 minutes. The filters were placed into autoradiography cassettes with Hyperfilm (Amersham) and placed at −80° C. overnight. The film was then developed, and the coordinates of P1 clones which hybridized to the probe were recorded. Bacterial stocks containing these positive P1 clones were obtained from Genome Systems Inc. and the DNA from these stocks was isolated (Qiagen Miniprep System, Qiagen, Chatsworth, Calif.).

An aliquot of DNA was digested with EcoRI, electrophoresed on a 0.9% agarose gel, and the bands migrating at approximately 2–3 kb were excised, purified, and subcloned into a plasmid (Bluescript-KSII, Stratagene) previously digested with EcoRI. DNA was isolated from bacteria containing inserts (Qiagen Miniprep System), digested with EcoRI, electrophoresed, transferred to nylon filters (Turboblotter, S&S, Keene, NH), and UV cross-linked (Stratagene, La Jolla, Calif.). These filters were then hybridized with the NcoI-NotI probe as described above to identify clones which contained ART sequences. A clone containing an approximately 2.3 kb EcoRI fragment was found to hybridize to the ART probe. DNA from this clone was then sequenced, and the nucleic acid sequence of this ART genomic DNA is shown in FIG. 1 (SEQ ID NO:4). When the sequence from this genomic clone was compared to the cDNA sequence obtained from adrenal gland and brain, the ART coding sequence was found to be divided into 3 exons. Furthermore, the 5' untranslated sequence present in the brain cDNA was found to be a separate exon, located 5' to these 3 coding exons. Therefore, the ART gene appears to be composed of three coding exons and a variably spliced untranslated exon.

It is possible that the smaller ART transcripts that were identified in Northern blots of peripheral tissues are due to the absence of this non-coding exon. Interestingly, mouse agouti is known to use alternatively-spliced non-coding exons during different phases of the hair-growth cycle.

Example III

Preparation of ART Peptides

A synthetic peptide containing amino acids 79–132 of ART was prepared using standard solid phase FMOC protection chemistry. The sequence of this peptide is set forth in FIG. 5 (SEQ ID NO:8). To refold the ART peptide, about 5.0 mg of lyophilized powder was dissolved in 25 ml of 20 mM Tris-HCl and 4M urea (pH 7.0). This mixture was stirred slowly overnight at room temperature. After stirring, the sample was concentrated in an Amicon (Beverly, Mass.) stirred cell using a cutoff membrane of 3 kDa. The final volume after concentration was about 1 ml. This sample was then diluted with about 15 ml of sterile 1×D-PBS (Gibco/ BRL, Grand Island, N.Y.), and was then reconcentrated to a final volume of about 1 ml. The stirred cell was rinsed twice with about 2 ml of D-PBS, and this 4 ml of solution was added to the sample. This sample solution, now about 5 ml, was concentrated further in an Amicon Centricon 3 device to a final volume of about 0.5 ml (equivalent to about 10 mg/ml). The sample was then sterile filtered in a Costar (Cambridge, Mass.) 0.22 μm Spinex filter device and stored at 4° C.

This peptide sample was administered to rats as described in Example V below.

Example IV

Cloning of Mouse ART Genomic DNA

A mouse liver tissue genomic library (Stratagene, La Jolla, Calif.) was screened for the mouse ART genomic DNA using the 600 bp a-$^{32}$P-dCTP labelled NcoI-NotI cDNA probe (see Example I) in RapidHyb buffer (Amersham, Arlington Heights, Ill.; catalog number RPN 1636) at about 65° C. for about 4 hours. The filters were then washed in 2×SSC containing 0.2% SDS at room temperature for 30 minutes, and then in 0.2×SSC containing 0.2% SDS at 65° C. for 30 minutes. The filters were placed into autoradiography cassettes with Hyperfilm (Amersham, Arlington Heights, Ill.) and placed at −80° C. overnight. The film was then developed, and one clone was identified as binding to the probe.

This clone, termed m-ARTg, was plaque purified using standard methods, the bacteria were lysed, and the DNA was then isolated using a Qiagen (Chatsworth, Calif.) Maxiprep column. The purified DNA was digested with XbaI, and an approximaately 2.8 kb fragment was found to hybridize with the human ART cDNA probe. This 2.8 kb fragment was subcloned into the vector pBlueScript (Stratagene, La Jolla, Calif.) and sequenced. The coding region of this sequence is set forth in FIG. 7. The splice donor/acceptor sites in this gene were found to be comparable to those in the human ART genomic DNA, indicating that the mouse ART gene also has three coding exons (2, 3, and 4) and one non-coding exon (exon 1). The predicted amino acid sequence of mouse ART is shown in FIG. 8. This sequence is about 81 percent identical to the human ART polypeptide sequence.

Example V

Feeding Behavior of Rats Treated With ART

Long-Evans male rats weighing 300–500 grams were chronically implanted in the brain with a 22 gauge cannula aimed at the lateral ventricle. The steriotaxic coordinates for the canulas were approximately: 0.8 mm anterior/posterior; 1.4 mm medial/lateral; and 3.5 mm dorsal/ventral. A 3.5 mm, 28 gauge stylet remained inside the implanted cannula until the animal was ready for an injection. ART peptide or control solutions were administered with a 28 gauge injector that extended about 1 mm beyond the tip of the cannula.

ART peptide was dissolved in PBS (pH about 7.0) and injected into the lateral ventricle at doses ranging from about 0.075 nmol to about 7.5 nmol in a volume of about 2 μl. Controls were PBS and an unfolded version of ART at about 7.5 nmol. Feeding measurements were taken from pre-weighed dishes containing a mixture of ground rodent chow, sugar, and condensed milk. (45%:28%:27%). Rats were offered this mixture along with their regular chow about 24 hours prior to injection. About one and one half hours prior to infusion, the regular chow was removed, but the rats were allowed to continue feeding on the sweetened mixture. Injections were done at 8:30 am or at 8:30 pm. Food intake was assesed by weighing the dishes over time at 90 minutes, 4 hours, 8 hours, 12 hours, and 24 hours after injection. 10–12 rats were used per group.

The results are shown in FIG. 10. As can be seen, those rats receiving folded ART increased their food intake as compared to controls. Further, there is a correlation between the amount of ART injected and the amount of food eaten by the rats.

---

We claim:

1. An isolated nucleic acid molecule, wherein the nucleic acid molecule is selected from the group consisting of:
   (a) the nucleic acid molecule of SEQ ID NO:4;
   (b) the nucleic acid molecule of SEQ ID NO:5;
   (c) the nucleic acid molecule of SEQ ID NO:6;
   (d) the nucleic acid molecule of SEQ ID NO:9;
   (e) a nucleic acid molecule encoding the polypeptide of SEQ ID NO:8;
   (f) a nucleic acid molecule encoding the polypeptide of SEQ ID NO:10;
   (g) a nucleic acid molecule encoding the polypeptide of SEQ ID NO:11; and
   (h) a nucleic acid molecule that encodes a polypeptide that has at least 80 percent sequence identity with the polypeptides of SEQ ID NO:7, SEQ ID NO:8, SEQ ID NO:10, or SEQ ID NO:11.

2. A vector comprising the nucleic acid molecule of claim 1.

3. A host cell comprising the vector of claim 2.

4. A process for producing a biologically active ART (Agouti Related Transcript) polypeptide comprising the steps of:
   (a) expressing a polypeptide encoded by a nucleic acid of claim 1 in a suitable host cell; and
   (b) isolating the polypeptide.

5. The process of claim 4 wherein the polypeptide is selected from the group consisting of: SEQ ID NO:7, SEQ ID NO:8, SEQ ID NO:10, and SEQ ID NO:11.

6. An isolated nucleic acid molecule that is the complement of the nucleic acid molecule of claim 1.

7. An isolated nucleic acid molecule comprising the nucleotide sequence set forth in SEQ ID NO:4.

8. A vector comprising the nucleic acid molecule of claim 7.

9. A host cell comprising the vector of claim 8.

10. An isolated nucleic acid molecule comprising the nucleotide sequence set forth in SEQ ID NO:5.

11. A vector comprising the nucleic acid molecule of claim 10.

12. A host cell comprising the vector of claim 11.

13. An isolated nucleic acid molecule comprising the nucleotide sequence set forth in SEQ ID NO:6.

14. A vector comprising the nucleic acid molecule of claim 13.

15. A host cell comprising the vector of claim 14.

16. An isolated nucleic acid molecule comprising the nucleotide sequence set forth in SEQ ID NO:9.

17. A vector comprising the nucleic acid molecule of claim 16.

18. A host cell comprising the vector of claim 17.

19. An isolated nucleic acid molecule encoding the polypeptide of SEQ ID NO:7.

20. A vector comprising the nucleic acid molecule of claim 19.

21. A host cell comprising the vector of claim 20.

22. An isolated nucleic acid molecule encoding the polypeptide of SEQ ID NO:8.

23. An isolated nucleic acid molecule encoding the polypeptide of SEQ ID NO:10.

24. An isolated nucleic acid molecule encoding the polypeptide of SEQ ID NO:11.

25. A vector comprising the nucleic acid molecule of claim 24.

26. A host cell comprising the vector of claim 25.

* * * * *

UNITED STATES PATENT AND TRADEMARK OFFICE
CERTIFICATE OF CORRECTION

PATENT NO. : 5,766,877
DATED : June 16, 1998
INVENTOR(S) : KEVIN LEE STARK and ROLAND LUETHY It is certified that error appears in the above-identified patent and that said Letters Patent is hereby corrected as shown below:

Column 14, line 60, change "30 kDa" to --1kDa--.

Signed and Sealed this

Twenty-seventh Day of October, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide"

( x i ) SEQUENCE DESCRIPTION: SEQ ID NO:1:

CCATCCTAAT ACGACTCACT ATAGGGC                        27

( 2 ) INFORMATION FOR SEQ ID NO:2:

( i ) SEQUENCE CHARACTERISTICS:
        ( A ) LENGTH: 22 base pairs ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Oligonucleotide"

( x i ) SEQUENCE DESCRIPTION: SEQ ID NO:2:

TAGCCCCGAC CCTGACGTTG GC                                                                          2 2

( 2 ) INFORMATION FOR SEQ ID NO:3:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Oligonucleotide"

( x i ) SEQUENCE DESCRIPTION: SEQ ID NO:3:

ACTCACTATA GGGCTCGAGC GGC                                                                         2 3

( 2 ) INFORMATION FOR SEQ ID NO:4:

( i ) SEQUENCE CHARACTERISTICS:
            ( A ) LENGTH: 2371 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| GAATTCTTGG | AAGCACAGGA | AACAACATGC | CACATAGGGG | TTGAGTAAGC | ATCTCTGGGG | 60 |
| CCACAAATTA | AATTAAGCTT | TCAGGGCCGC | CTGCCTTGTT | ATTGCTAATG | GTTCTAGCCC | 120 |
| TGCTCAGCTC | CTAGGTCCCT | GTCCTGTGGA | AATTTGTGGA | CCCTGGGCAC | CCTCTCTTGC | 180 |
| TCCCAAATTT | TAATCGGCTC | CTGGAAACCT | CACCCCAAAT | TGGAGATAGG | CACTCCTCTT | 240 |
| GTAGAACAAA | AGGCTCAGGT | TCAGGGAGTG | AGGGCCTGAA | CTGTGCCCCC | ACCCTCCAGG | 300 |
| AAGGGTCCTT | CACGGCCTGG | CTGCAGGGAT | CAGTCACGTG | TGGCCCTTCA | TTAGGCCCTG | 360 |
| CCATATAAGC | CAAGGGCACG | GGGTGGCCGG | GAACTCTCTA | GGCAAGAATC | CCGGAGGCAG | 420 |
| AGGTGAGTCC | TCAGGTTGGG | CAGGGACTCC | TCCTCTCTGT | GGGGTCTCTA | TCTGGGCACC | 480 |
| TAGAGGGGAC | TCCAAGGATA | AGGAGGGACT | AAGTGGTACA | TCTTCCTGCT | GAGCCAGGCC | 540 |
| ATGCTGACCG | CAGCGGTGCT | GAGCTGTGCC | CTGCTGCTGG | CACTGCCTGC | CACGCGAGGA | 600 |
| GCCCAGATGG | GCTTGGCCCC | CATGGAGGGC | ATCAGAAGGC | CTGACCAGGC | CCTGCTCCCA | 660 |
| GAGCTCCCAG | GTCAGTGTGA | GCAAGGGTGG | GACTGGGCGG | GGCCTGAATA | CCCTCTGGCC | 720 |
| ACAAATAGTC | TCCCCTGGCA | TAAACCCTCT | TTCTCCCTTC | CCAAACCCTC | CCCTGGGAGG | 780 |
| TGGGTGCTTT | GTGCATGGGG | GTTCCTGCCC | TCACATCCTC | TGCCCCAGGC | CTGGGCCTGC | 840 |
| GGGCCCCACT | GAAGAAGACA | ACTGCAGAAC | AGGCAGAAGA | GGATCTGTTG | CAGGAGGCTC | 900 |
| AGGCCTTGGC | AGAGGTAACT | GCTCAGGGAA | AAGGGTAAGG | TGGTGGCCCT | TGGGAGGGGG | 960 |
| CATTGGGTAT | TAGCTCCTCT | CCCCAGCTCC | AAACTCCCTC | ACCAGCGACG | ACACTACCGA | 1020 |
| CCACCCCTTC | CCATGCTCCA | CTGCCATCCT | GCACAGGTTG | GGACAGGTAA | GATCCCTGGA | 1080 |
| TCTGTCTTTA | GAGGCCTGTG | CTGGTTCCCC | ACCCCTGCAG | GTACTAGACC | TGCAGGACCG | 1140 |
| CGAGCCCCGC | TCCTCACGTC | GCTGCGTAAG | GCTGCATGAG | TCCTGCCTGG | GACAGCAGGT | 1200 |

```
GCCTTGCTGT  GACCCATGTG  CCACGTGCTA  CTGCCGCTTC  TTCAATGCCT  TCTGCTACTG    1260
CCGCAAGCTG  GGTACTGCCA  TGAATCCCTG  CAGCCGCACC  TAGCTGGCCA  ACGTCAGGGT    1320
CGGGGCTAGG  GTAGGGGCAA  GGAAACTCGA  ATAAAGGATG  GGACCAACCC  CAAGGCTGTG    1380
GTTATTTCAA  ACGTGGCCGT  CAAAGGAGGG  AGGGTTCATG  GAGGGGGTGG  GAGTGTCACC    1440
AAGCCAAGAA  ACCACACATA  CTCTTATCCC  AGGGCCTGGG  CTACCCTATC  ATAGGAGGCA    1500
CATACACGGG  CGCTTTTAGG  GGTCCTGGTG  CCCCTGGGAA  AAATAGAGAA  GAGCCGCACT    1560
CCAGCTTTCG  AAAATCTTGT  ACAGCAAGTG  CGGGGAACGC  AGGACGCAGC  GTGGCACAGG    1620
GGCTATCACT  CCTGGCTAAC  AAATAAGCCT  TAGGCTCCAG  GGCTTGCTGC  TACTTCCACG    1680
CAAAGCCTGC  CCCTCATCCT  GTTACCAGAG  GGAAGGCCAG  GAGTGTGCGT  TGTTCAGGTC    1740
CTTAGCGTTT  CGAACAAAGA  ATTGAACAAA  ACCCAGAAAG  TAACAAACGA  ATGACACACA    1800
GGAAGGAAGC  AGACAGCTGG  GATTTGTTAA  AGCGAGAAAG  CACTACGCAG  GGTGGGAGTG    1860
GGCCTGAGCA  AGAGGCTGAA  GGGGCTCAGT  TACAAAGTTT  TCCGGGTTTT  AAGTACTCCT    1920
TTTGCGGTCC  CTGTCCGTTA  CCCCTTATCT  GGATGAAGGG  TTTGGTCCAT  GGCTAATTAA    1980
TCCATTTATG  CCTGAGGTTG  CAATCTTTTT  GAATTTTGC   AATCAGACCT  TGGCCATGAC    2040
CTTGAGCAGT  AGGATATAAA  TAACTCCCAT  ATGCTTAGCG  TTCCAATAAT  GGAACACAAG    2100
GCATAAATGG  GGCTAAGGTG  AATTGGCGCC  CTATGCAGAT  GAAGGGATGG  CCCGTGCTTG    2160
GCCCGCAGCC  AATCCAAGGC  ACTCTCCCTT  TCAACTGAGA  CGTGGTGGAA  GGGGAGGGT     2220
TGTGGGGACA  GTGGCCTTTG  ATCCTTTGTT  ACTTGGACAT  GGGGAGATGG  GGTTTTTCTT    2280
TTTGGTTTAG  CTTTAGTAAG  CTCGCCTTAG  TTGGCCTCCG  GTTCCTGCC   CCCAGACCTT    2340
GGTGTTTTCC  CTTGATTCAG  CTTCAGAATT  C                                     2371
```

( 2 ) INFORMATION FOR SEQ ID NO:5:

( i ) SEQUENCE CHARACTERISTICS:
        ( A ) LENGTH: 830 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GGGCCCTCTA  GATGCATGCT  CGAGCGGCCG  CCAGTGTGAT  GGATATCTGC  AGAATTCGGC     60
TTGGTCCCTG  TCCTGTGGAA  ATTTGTGGAC  CCTGGGCACC  CTCTCTTGCT  CCCAAATTTT    120
AATCGGCTCC  TGGAAACCTC  ACCCCAAATT  GGAGATAGGC  ACTCCTCTTG  TAGAACAAAA    180
GGCTCAGGTT  CAGGGAGTGA  GGGCCTGAAC  TGTGCCCCA   CCCTCCAGGA  AGGGTCCTTC    240
ACGGCCTGGC  TGCAGGGATC  AGTCACGTGT  GGCCCTTCAT  TAGGCCCTGC  CATATAAGCC    300
AAAGGCACGG  GGTGGCCGGG  AACTCTCTAG  GCAAGAATCC  CGGAGGCAGA  GGCCATGCTG    360
ACCGCAGCGG  TGCTGAGCTG  TGCCCTGCTG  CTGGCACTGC  CTGCCACGCG  AGGAGCCCAG    420
ATGGGCTTGG  CCCCCATGGA  GGGCATCAGA  AGGCCTGACC  AGGCCCTGCT  CCCAGAGCTC    480
CCAGGCCTGG  GCCTGCGGGC  CCCACTGAAG  AAGACAACTG  CAGAACAGGC  AGAAGAGGAT    540
CTGTTGCAGG  AGGCTCAGGC  CTTGGCAGAG  GTACTAGACC  TGCAGGACCG  CGAGCCCGC    600
TCCTCACGTC  GCTGCGTAAG  GCTGCATGAG  TCCTGCCTGG  GACAGCAGGT  GCCTTGCTGT    660
GACCCATGTG  CCACGTGCTA  CTGCCGCTTC  TTCAATGCCT  TCTGCTACTG  CCGCAAGCTG    720
GGTACTGCCA  TGAATCCCTG  CAGCCGCACC  TAGCTGGCCA  ACGTCAGGGT  CGGGGCTAGG    780
GTAGGGGCAA  GGAAACTCGA  ATAAAGGATG  GGACCAACAA  AAAAAAAAA                 830
```

( 2 ) INFORMATION FOR SEQ ID NO:6:

( i ) SEQUENCE CHARACTERISTICS:
      ( A ) LENGTH: 479 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:6:

```
GCCATGCTGA CCGCAGCGGT GCTGAGCTGT GCCCTGCTGC TGGCACTGCC TGCCACGCGA       60
GGAGCCCAGA TGGGCTTGGC CCCCATGGAG GGCATCAGAA GGCCTGACCA GGCCCTGCTC      120
CCAGAGCTCC CAGGCCTGGG CCTGCGGGCC CCACTGAAGA AGACAACTGC AGAACAGGCA      180
GAAGAGGATC TGTTGCAGGA GGCTCAGGCC TTGGCAGAGG TACTAGACCT GCAGGACCGC      240
GAGCCCCGCT CCTCACGTCG CTGCGTAAGG CTGCATGAGT CCTGCCTGGG ACAGCAGGTG      300
CCTTGCTGTG ACCCATGTGC CACGTGCTAC TGCCGCTTCT TCAATGCCTT CTGCTACTGC      360
CGCAAGCTGG GTACTGCCAT GAATCCCTGC AGCCGCACCT AGCTGGCCAA CGTCAGGGTC      420
GGGGCTAGGG TAGGGGCAAG GAAACTCGAA TAAAGGATGG GACCAACAAA AAAAAAAA       479
```

( 2 ) INFORMATION FOR SEQ ID NO:7:

( i ) SEQUENCE CHARACTERISTICS:
      ( A ) LENGTH: 132 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:7:

```
Met Leu Thr Ala Ala Val Leu Ser Cys Ala Leu Leu Leu Ala Leu Pro
 1               5                  10                  15
Ala Thr Arg Gly Ala Gln Met Gly Leu Ala Pro Met Glu Gly Ile Arg
            20                  25                  30
Arg Pro Asp Gln Ala Leu Leu Pro Glu Leu Pro Gly Leu Gly Leu Arg
        35                  40                  45
Ala Pro Leu Lys Lys Thr Thr Ala Glu Gln Ala Glu Glu Asp Leu Leu
    50                  55                  60
Gln Glu Ala Gln Ala Leu Ala Glu Val Leu Asp Leu Gln Asp Arg Glu
65                  70                  75                  80
Pro Arg Ser Ser Arg Arg Cys Val Arg Leu His Glu Ser Cys Leu Gly
                85                  90                  95
Gln Gln Val Pro Cys Cys Asp Pro Cys Ala Thr Cys Tyr Cys Arg Phe
               100                 105                 110
Phe Asn Ala Phe Cys Tyr Cys Arg Lys Leu Gly Thr Ala Met Asn Pro
           115                 120                 125
Cys Ser Arg Thr
       130
```

( 2 ) INFORMATION FOR SEQ ID NO:8:

( i ) SEQUENCE CHARACTERISTICS:
      ( A ) LENGTH: 54 amino acids
      ( B ) TYPE: amino acid
      ( C ) STRANDEDNESS: single
      ( D ) TOPOLOGY: linear ( i i ) MOLECULE TYPE: protein (x i) SEQUENCE DESCRIPTION: SEQ ID NO:8:

| Arg | Glu | Pro | Arg | Ser | Ser | Arg | Arg | Cys | Val | Arg | Leu | His | Glu | Ser | Cys |
|---|---|---|---|---|---|---|---|---|---|---|---|---|---|---|---|
| 1 | | | | 5 | | | | | 10 | | | | | 15 | |

| Leu | Gly | Gln | Gln | Val | Pro | Cys | Cys | Asp | Pro | Cys | Ala | Thr | Cys | Tyr | Cys |
|---|---|---|---|---|---|---|---|---|---|---|---|---|---|---|---|
| | | | 20 | | | | | 25 | | | | | 30 | | |

| Arg | Phe | Phe | Asn | Ala | Phe | Cys | Tyr | Cys | Arg | Lys | Leu | Gly | Thr | Ala | Met |
|---|---|---|---|---|---|---|---|---|---|---|---|---|---|---|---|
| | | 35 | | | | | 40 | | | | | 45 | | | |

| Asn | Pro | Cys | Ser | Arg | Thr |
|---|---|---|---|---|---|
| | 50 | | | | |

(2) INFORMATION FOR SEQ ID NO:9:

(i) SEQUENCE CHARACTERISTICS:
(A) LENGTH: 734 base pairs
(B) TYPE: nucleic acid
(C) STRANDEDNESS: single
(D) TOPOLOGY: linear (ii) MOLECULE TYPE: DNA (genomic)

(x i) SEQUENCE DESCRIPTION: SEQ ID NO:9:

| ATGCTGACTG | CAATGTTGCT | GAGTTGTGTT | CTGCTGTTGG | CACTGCCTCC | CACACTGGGG | 60 |
|---|---|---|---|---|---|---|
| GTCCAGATGG | GCGTGGCTCC | ACTGAAGGGC | ATCAGAAGGC | CTGACCAGGC | TCTGTTCCCA | 120 |
| GAGTTCCCAG | GTGAGTATGG | TCAGGTTGGG | GATATGTGGG | GCAACGACCA | TTGCTGGCCA | 180 |
| CAGACCTGCC | CGCCCAGGCT | TAGACCTCCT | TCCCCAATCC | CAATCCCAAC | CTAGGGAGGT | 240 |
| GGGTACTTGG | TGCATGGTGG | GTGTGGCCCT | CACATCTTCT | GCCCCAGGTC | TAAGTCTGAA | 300 |
| TGGCCTCAAG | AAGACAACTG | CAGACCGAGC | AGAAGAAGTT | CTGCTGCAGA | AGGCAGAAGC | 360 |
| TTTGGCGGAG | GTAACTCATT | AGGGAAAGGG | ATAAAGTAGA | AGGTAGGGCG | CATCAGATAC | 420 |
| CATCATCTCT | CCCCACTTCC | GGATTACCCA | ACCTGGGCAG | AACTGCAGCC | CCTCCCTGAC | 480 |
| CTCAGTCCAC | TGCCACCCTA | CTGGGGTCGG | GGTTTGAGAG | TTTCCTGAAC | CTTATTCCCC | 540 |
| TACGAATGCA | GGTGCTAGAT | CCACAGAACC | GCGAGTCTCG | TTCTCCGCGT | CGCTGTGTAA | 600 |
| GGCTGCACGA | GTCCTGCTTG | GGACAGCAGG | TACCTTGCTG | CGACCCGTGC | GCTACGTGCT | 660 |
| ACTGCCGCTT | CTTCAATGCC | TTTTGCTACT | GCCGCAAGCT | GGGTACGGCC | ACGAACCTCT | 720 |
| GTAGTCGCAC | CTAG | | | | | 734 |

(2) INFORMATION FOR SEQ ID NO:10:

(i) SEQUENCE CHARACTERISTICS:
(A) LENGTH: 131 amino acids
(B) TYPE: amino acid
(C) STRANDEDNESS: single
(D) TOPOLOGY: linear (ii) MOLECULE TYPE: protein (x i) SEQUENCE DESCRIPTION: SEQ ID NO:10:

| Met | Leu | Thr | Ala | Met | Leu | Leu | Ser | Cys | Val | Leu | Leu | Leu | Ala | Leu | Pro |
|---|---|---|---|---|---|---|---|---|---|---|---|---|---|---|---|
| 1 | | | | 5 | | | | | 10 | | | | | 15 | |

| Pro | Thr | Leu | Gly | Val | Gln | Met | Gly | Val | Ala | Pro | Leu | Lys | Gly | Ile | Arg |
|---|---|---|---|---|---|---|---|---|---|---|---|---|---|---|---|
| | | | 20 | | | | | 25 | | | | | 30 | | |

| Arg | Pro | Asp | Gln | Ala | Leu | Phe | Pro | Glu | Phe | Pro | Gly | Leu | Ser | Leu | Asn |
|---|---|---|---|---|---|---|---|---|---|---|---|---|---|---|---|
| | | | 35 | | | | | 40 | | | | | 45 | | |

| Gly | Leu | Lys | Lys | Thr | Thr | Ala | Asp | Arg | Ala | Glu | Glu | Val | Leu | Leu | Gln |
|---|---|---|---|---|---|---|---|---|---|---|---|---|---|---|---|
| | | 50 | | | | | 55 | | | | | 60 | | | |

| Lys | Ala | Glu | Ala | Leu | Ala | Glu | Val | Leu | Asp | Pro | Gln | Asn | Arg | Glu | Ser |

```
                65                      70                      75                      80
Arg Ser Pro Arg Arg Cys Val Arg Leu His Glu Ser Cys Leu Gly Gln
                85                      90                      95

Gln Val Pro Cys Cys Asp Pro Cys Ala Thr Cys Tyr Cys Arg Phe Phe
            100             105                     110

Asn Ala Phe Cys Tyr Cys Arg Lys Leu Gly Thr Ala Thr Asn Leu Cys
        115                 120                 125

Ser Arg Thr
    130
```

( 2 ) INFORMATION FOR SEQ ID NO:11:

( i ) SEQUENCE CHARACTERISTICS:
        ( A ) LENGTH: 132 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met Leu Thr Ala Ala Val Leu Ser Cys Ala Leu Leu Leu Ala Leu Pro
1               5                       10                      15

Ala Thr Arg Gly Ala Gln Met Gly Leu Ala Pro Met Glu Gly Ile Arg
            20                      25                      30

Arg Pro Asp Gln Ala Leu Leu Pro Glu Leu Pro Gly Pro Gly Leu Arg
        35                      40                      45

Ala Pro Leu Lys Lys Thr Thr Ala Glu Gln Ala Glu Glu Asp Leu Leu
    50                      55                      60

Gln Glu Ala Gln Ala Leu Ala Glu Val Leu Asp Leu Gln Asp Arg Glu
65                      70                      75                      80

Pro Arg Ser Ser Arg Arg Cys Val Arg Leu His Glu Ser Cys Leu Gly
                85                      90                      95

Gln Gln Val Pro Cys Cys Asp Pro Cys Ala Thr Cys Tyr Cys Arg Phe
            100                     105                     110

Phe Asn Ala Phe Cys Tyr Cys Arg Lys Leu Gly Thr Ala Met Asn Pro
        115                     120                     125

Cys Ser Arg Thr
    130
```